(12) United States Patent
Suzuki

(10) Patent No.: US 12,738,028 B2
(45) Date of Patent: Sep. 15, 2026

(54) INFORMATION PROCESSING APPARATUS, INFORMATION PROCESSING METHOD, IMAGING DEVICE, VEHICLE DEVICE, AND MEDICAL ROBOT DEVICE

(71) Applicant: SONY GROUP CORPORATION, Tokyo (JP)

(72) Inventor: Kenji Suzuki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 435 days.

(21) Appl. No.: 18/255,170

(22) PCT Filed: Oct. 14, 2021

(86) PCT No.: PCT/JP2021/038146
§ 371 (c)(1),
(2) Date: May 31, 2023

(87) PCT Pub. No.: WO2022/123907
PCT Pub. Date: Jun. 16, 2022

(65) Prior Publication Data

US 2024/0005643 A1 Jan. 4, 2024

(30) Foreign Application Priority Data

Dec. 9, 2020 (JP) ................................ 2020-204550

(51) Int. Cl.
*G06V 10/774* (2022.01)
*A61B 34/32* (2016.01)
(Continued)

(52) U.S. Cl.
CPC ............ *G06V 10/774* (2022.01); *A61B 34/32* (2016.02); *G06V 20/56* (2022.01);
(Continued)

(58) Field of Classification Search
None
See application file for complete search history.

(56) References Cited

U.S. PATENT DOCUMENTS 10,783,401 B1 * 9/2020 Jiang .................... G06V 10/776
2019/0262084 A1 * 8/2019 Roh ....................... G16H 20/40
(Continued)

FOREIGN PATENT DOCUMENTS

JP 2018-072893 A 5/2018
JP 2019-076699 A 5/2019
(Continued)

OTHER PUBLICATIONS

International Search Report and Written Opinion of PCT Application No. PCT/JP2021/038146, issued on Dec. 14, 2021, 16 pages of ISRWO.

(Continued)

*Primary Examiner* — Leon Viet Q Nguyen
(74) *Attorney, Agent, or Firm* — CHIP LAW GROUP

(57) ABSTRACT

There is provided an information processing apparatus for artificially increasing data of a minority attribute to generate learning data for making fair determination on each piece of input data. The information processing apparatus includes a data holding unit configured to hold first learning data to be used for learning a machine learning model an acquisition unit configured to acquire information regarding bias of the learning data a data generation unit configured to generate second learning data by using data included in the learning data on the basis of the information regarding bias and a learning unit configured to learn the machine learning model by using the first learning data and the second learning data.

10 Claims, 17 Drawing Sheets

(51) Int. Cl.

| | |
|---|---|
| ***G06V 20/56*** | (2022.01) |
| *A61B 34/20* | (2016.01) |
| *B60W 30/00* | (2006.01) |
| *B60W 60/00* | (2020.01) |
| *G06V 10/764* | (2022.01) |
| *G06V 10/82* | (2022.01) |

(52) U.S. Cl.

CPC ...... *A61B 2034/2065* (2016.02); *B60W 30/00* (2013.01); *B60W 60/00* (2020.02); *B60W 2420/403* (2013.01); *G06V 10/764* (2022.01); *G06V 10/82* (2022.01); *G06V 2201/03* (2022.01)

(56) References Cited

U.S. PATENT DOCUMENTS

| | | | | |
|---|---|---|---|---|
| 2020/0250304 | A1 | 8/2020 | Kruus et al. | |
| 2021/0019641 | A1* | 1/2021 | Park | G10L 17/04 |
| 2021/0110439 | A1* | 4/2021 | Jayne | G06V 10/82 |
| 2021/0272016 | A1* | 9/2021 | Veshchikov | G06F 11/0721 |
| 2021/0406712 | A1* | 12/2021 | Bhide | G06N 3/08 |
| 2022/0101146 | A1* | 3/2022 | el Kaliouby | G06N 3/0455 |

FOREIGN PATENT DOCUMENTS

| | | | |
|---|---|---|---|
| JP | 2019-200769 | A | 11/2019 |
| JP | 6635221 | B1 | 1/2020 |
| JP | 2020-534594 | A | 11/2020 |
| JP | 6779491 | B1 | 11/2020 |

OTHER PUBLICATIONS

Toshiaki Inoue, "A scene recognition method using dashcams for reducing traffic accident risks", Pioneer R&D, Oct. 31, 2020, 05 pages.

Hiroyuki Umeda, "Transfer learning and overfitting", The Basics of AI Every Engineer Needs to Know: Easy Explanation of Machine Learning, Statistics, and Algorithms, Impress Corporation, Jan. 21, 2019, pp. 80-84.

Sun, et al, "Training Augmentation with Adversarial Examples for Robust Speech Recognition", arxiv.org, Jun. 17, 2018, 05 pages.

Goodfellow, et al., "Explaining and Harnessing Adversarial Examples", arxiv.org, Mar. 20, 2015, 12 pages.

* cited by examiner 201
202
203
$x$
$+\varepsilon\times$
$\epsilon sign(\nabla_x J(\theta, x, y))$
=
$x + \epsilon sign(\nabla_x J(\theta, x, y))$

*FIG. 7*

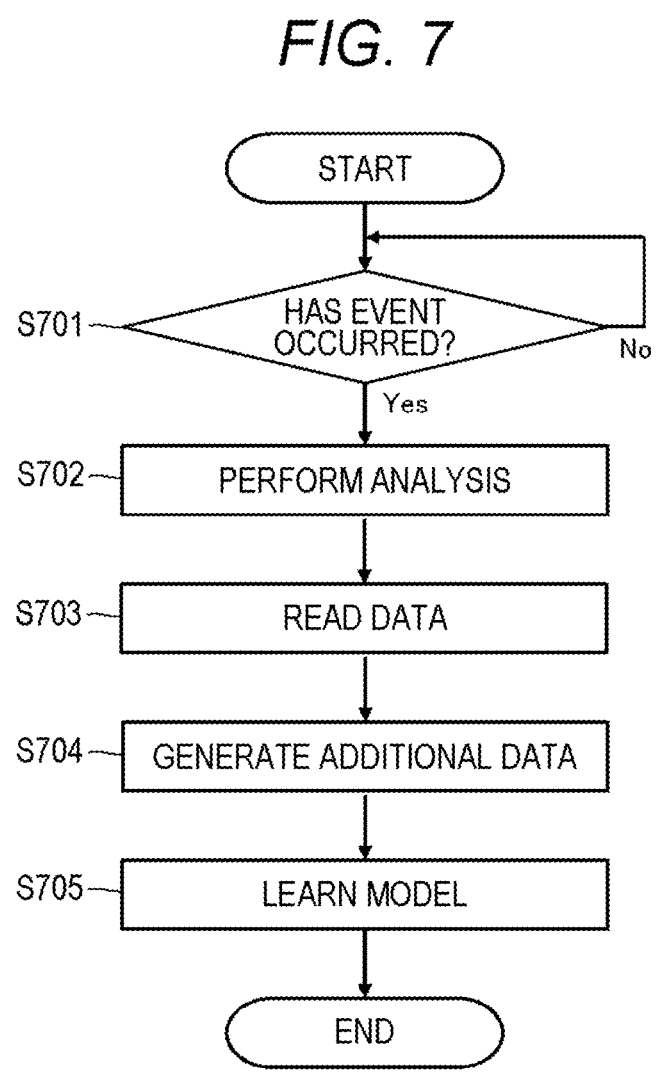

START
S701 HAS EVENT OCCURRED?
No
Yes
S702 PERFORM ANALYSIS
S703 READ DATA
S704 GENERATE ADDITIONAL DATA
S705 LEARN MODEL
END

FIG. 10

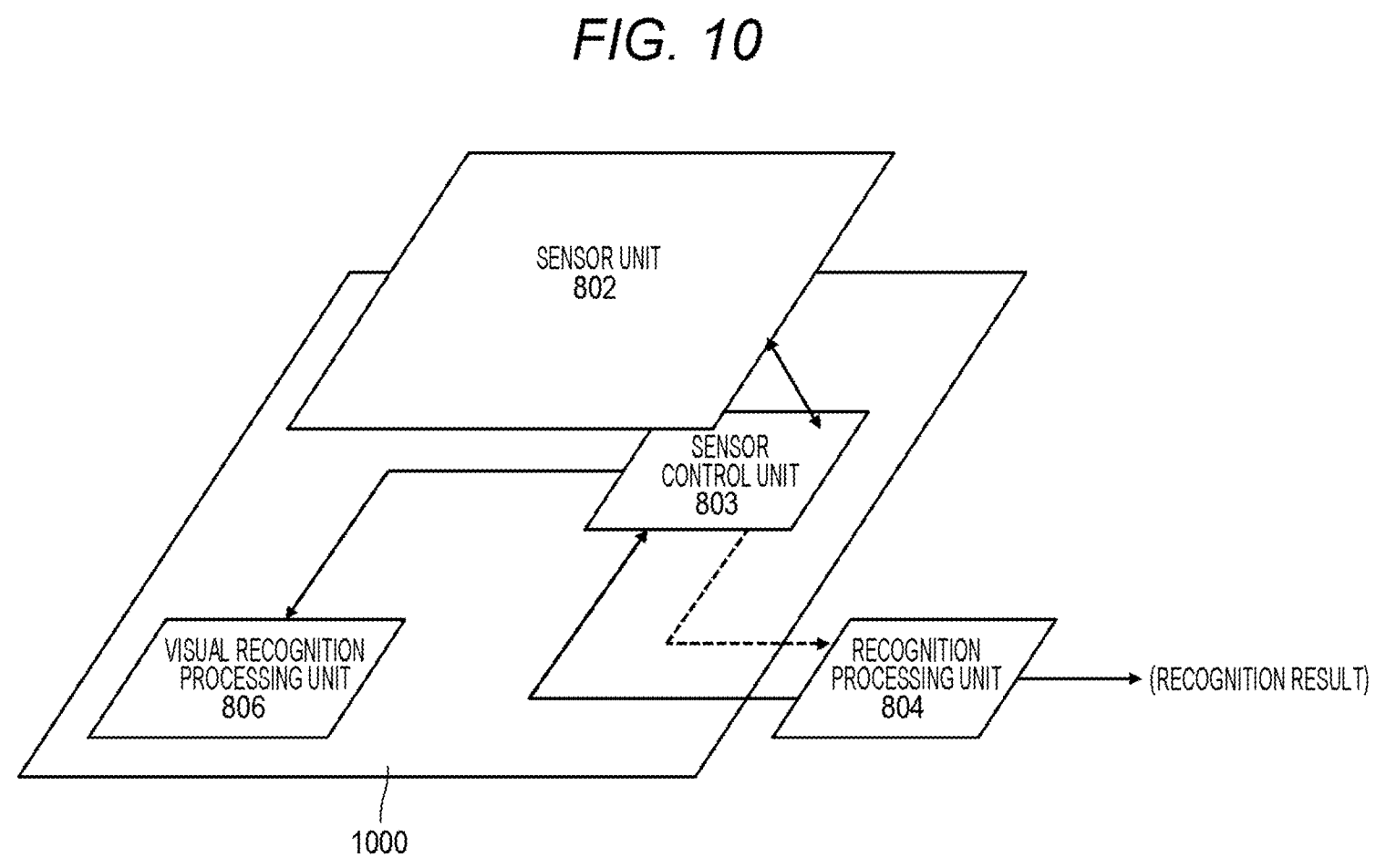

SENSOR UNIT
802

SENSOR
CONTROL UNIT
803

RECOGNITION
PROCESSING UNIT
804

(RECOGNITION RESULT)

VISUAL RECOGNITION
PROCESSING UNIT
806

1000

1201
1202
1203
1200
PIXEL UNIT
1211
MEMORY UNIT 1212
LOGIC UNIT 1213
1201
1203
1202

PIXEL ARRAY UNIT 1301
VERTICAL SCANNING UNIT 1302
AD CONVERSION UNIT 1303
HORIZONTAL SCANNING UNIT 1304
1305
1310
VSL
ADC 1311
REFERENCE SIGNAL GENERATION UNIT 1312
CONTROL UNIT 1306
SIGNAL PROCESSING UNIT 1307
PIXEL SIGNAL
IMAGING CONTROL SIGNAL

SIGNAL PROCESSING UNIT 1503
DEVELOPMENT PROCESSING UNIT 1604
DIGITAL GAIN PROCESSING
GAMMA PROCESSING
DETECTION UNIT 1605
COMPARISON UNIT 1606
Ref
CONTROL UNIT 1505
IMAGE SENSOR 1502
SHUTTER 1601
ELEMENT UNIT 1602
ANALOG GAIN PROCESSING UNIT 1603
LENS 1501
1500

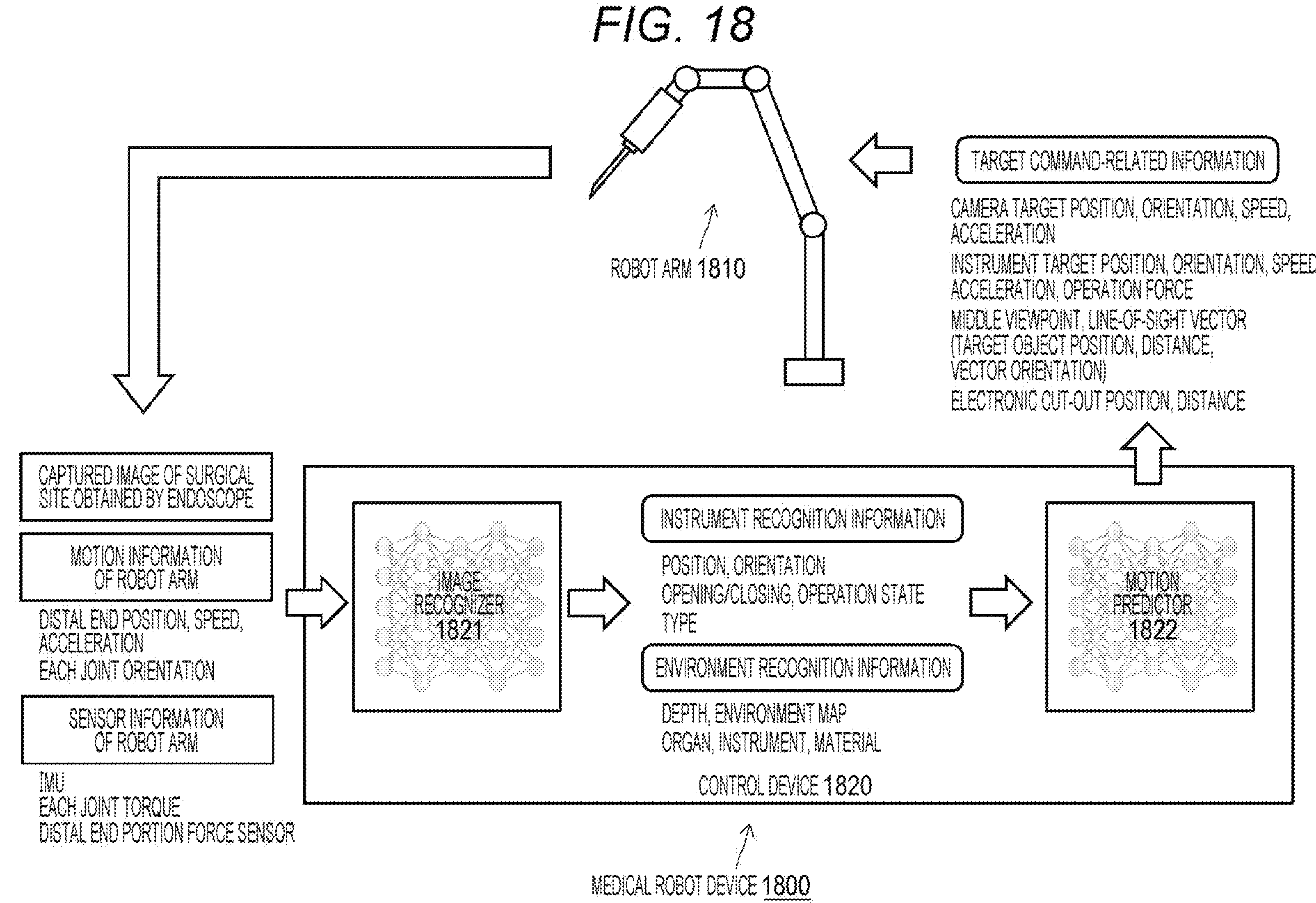
FIG. 18
ROBOT ARM 1810
TARGET COMMAND-RELATED INFORMATION
CAMERA TARGET POSITION, ORIENTATION, SPEED, ACCELERATION
INSTRUMENT TARGET POSITION, ORIENTATION, SPEED, ACCELERATION, OPERATION FORCE
MIDDLE VIEWPOINT, LINE-OF-SIGHT VECTOR (TARGET OBJECT POSITION, DISTANCE, VECTOR ORIENTATION)
ELECTRONIC CUT-OUT POSITION, DISTANCE
CAPTURED IMAGE OF SURGICAL SITE OBTAINED BY ENDOSCOPE
MOTION INFORMATION OF ROBOT ARM
DISTAL END POSITION, SPEED, ACCELERATION
EACH JOINT ORIENTATION
SENSOR INFORMATION OF ROBOT ARM
IMU
EACH JOINT TORQUE
DISTAL END PORTION FORCE SENSOR
IMAGE RECOGNIZER 1821
INSTRUMENT RECOGNITION INFORMATION
POSITION, ORIENTATION
OPENING/CLOSING, OPERATION STATE
TYPE
ENVIRONMENT RECOGNITION INFORMATION
DEPTH, ENVIRONMENT MAP
ORGAN, INSTRUMENT, MATERIAL
MOTION PREDICTOR 1822
CONTROL DEVICE 1820
MEDICAL ROBOT DEVICE 1800

INFORMATION PROCESSING APPARATUS, INFORMATION PROCESSING METHOD, IMAGING DEVICE, VEHICLE DEVICE, AND MEDICAL ROBOT DEVICE

CROSS REFERENCE TO RELATED APPLICATIONS

This application is a U.S. National Phase of International Patent Application No. PCT/JP2021/038146 filed on Oct. 14, 2021, which claims priority benefit of Japanese Patent Application No. JP 2020-204550 filed in the Japan Patent Office on Dec. 9, 2020. Each of the above-referenced applications is hereby incorporated herein by reference in its entirety.

TECHNICAL FIELD

The technology disclosed in the present specification (hereinafter, "the present disclosure") relates to an information processing apparatus and an information processing method for performing processing related to learning data, a computer program, an imaging device, a vehicle device, and a medical robot device.

BACKGROUND ART

Artificial intelligence can analyze and estimate enormous data, and is utilized for, for example, image recognition, voice recognition, and natural language processing. The artificial intelligence is realized by performing learning on a machine learning model configured by a neural network or the like. For example, there has been proposed an imaging device including a recognition unit that performs recognition processing using a learned model, and outputting a recognition result for a pixel signal (see Patent Document 1).

By performing deep learning using a huge amount of learning data sets, it is possible to obtain artificial intelligence that realizes inference exceeding human ability (face recognition, object recognition, and the like). However, if there is bias in the learning data, there is a concern that the artificial intelligence makes unfair determination with bias. For example, when learning a machine learning model that classifies images of persons, if learning of image classification is performed using data with biased attributes such as age, gender, race, and ethnicity, there is a possibility that the learning model cannot make fair determination, such as outputting a disadvantageous result for a minority attribute.

CITATION LIST

Patent Document

Patent Document 1: Japanese Patent No. 6635221
Patent Document 2: Japanese Patent Application Laid-Open No. 2018-72893
Non Patent Document
Non Patent Document 1: Goodfellow et al. "Explaining and Harnessing Adversarial Examples." (2015) ICLR.

SUMMARY OF THE INVENTION

Problems to be Solved by the Invention

An object of the present disclosure is to provide an information processing apparatus and an information processing method for performing processing related to data for learning a model to enable fair determination on each piece of input data, a computer program, an imaging device, a vehicle device, and a medical robot device.

Solutions to Problems

The present disclosure has been made in view of the problem described above, and a first aspect thereof is an information processing apparatus including:

- a data holding unit configured to hold first learning data to be used for learning of a machine learning model;
- an acquisition unit configured to acquire information regarding bias of the learning data;
- a data generation unit configured to generate second learning data by using data included in the learning data on the basis of the information regarding bias; and
- a learning unit configured to learn the machine learning model by using the first learning data and the second learning data.

The acquisition unit acquires information indicating a minority attribute in the first learning data. Then, from data of the minority attribute included in the first learning data, the data generation unit generates second learning data of the same attribute.

The data generation unit generates Adversarial Example to be second learning data, from the data of the minority attribute included in the learning data. For example, the data generation unit generates the Adversarial Example on the basis of Fast Gradient Sign Method.

Furthermore, a second aspect of the present disclosure is an information processing method including:

- a step of inputting first learning data to be used for learning of a machine learning model;
- a step of acquiring information regarding bias of the learning data;
- a step of generating second learning data by using data included in the learning data on the basis of the information regarding bias; and
- a step of learning the machine learning model by using the first learning data and the second learning data.

Furthermore, a third aspect of the present disclosure is a computer program described in a computer-readable format to cause a computer to function as:

- a data holding unit configured to hold first learning data to be used for learning of a machine learning model;
- an acquisition unit configured to acquire information regarding bias of the learning data;
- a data generation unit configured to generate second learning data by using data included in the learning data on the basis of the information regarding bias; and
- a learning unit configured to learn the machine learning model by using the first learning data and the second learning data.

The computer program according to the third aspect of the present disclosure is obtained by defining a computer program described in a computer-readable format so as to implement predetermined processing on a computer. In other words, by installing the computer program according to the claims of the present application in a computer, a cooperative action is exhibited on the computer, and operation and effects similar to those of the information processing apparatus according to the first aspect of the present disclosure can be obtained.

Furthermore, a fourth aspect of the present disclosure is an imaging device including:

an imaging unit configured to capture an image; and a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

Furthermore, a fifth aspect of the present disclosure is a vehicle device including:

an imaging device including an imaging unit configured to capture an image around a vehicle, and a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

Furthermore, a sixth aspect of the present disclosure is a medical robot device including:

an imaging device including an imaging unit configured to capture an image around a surgical site, and a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

Effects of the Invention

According to the present disclosure, it is possible to provide an information processing apparatus and an information processing method for artificially increasing data of a minority attribute to generate learning data for making fair determination on each piece of input data, a computer program, an imaging device, a vehicle device, and a medical robot device.

Note that the effects described in the present specification are merely examples, and the effects brought by the present disclosure are not limited thereto. Furthermore, the present disclosure may further provide additional effects in addition to the effects described above.

Other objects, features, and advantages of the present disclosure will become apparent from the detailed description based on the embodiment described later and the accompanying drawings.

BRIEF DESCRIPTION OF DRAWINGS

FIG. 7 is a flowchart illustrating another operation example in the learning phase of the learning system 100.

FIG. 10 is a diagram illustrating another hardware implementation example of the imaging device 800.

FIG. 18 is a view illustrating a configuration example of a medical robot device 1800.

MODE FOR CARRYING OUT THE INVENTION

Figure 1:
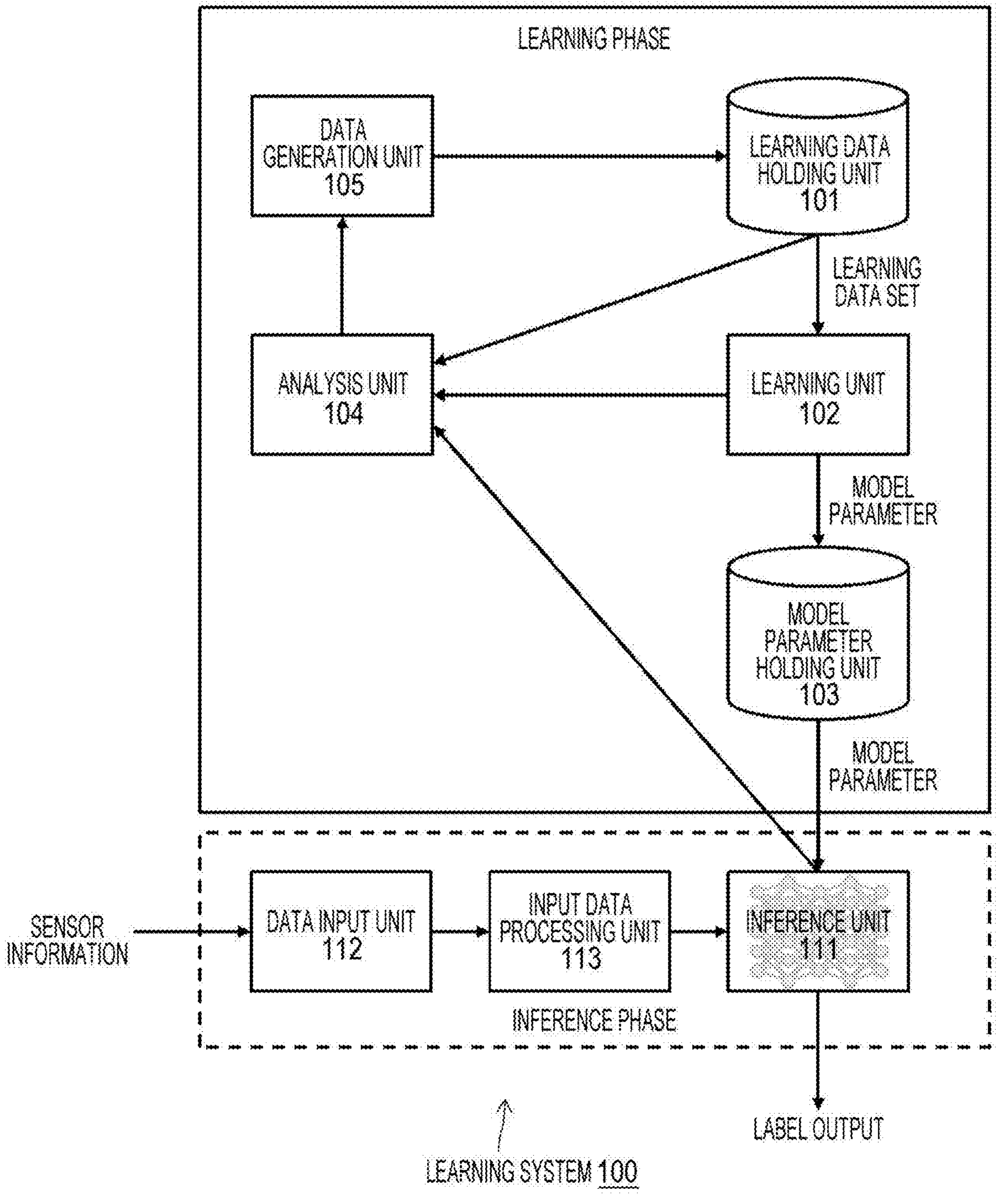
FIG. 1 is a diagram illustrating a functional configuration example of a learning system 100.

Hereinafter, the present disclosure will be described in the following order with reference to the drawings.

A. Overview
B. Learning system
C. Addition of learning data
D. About fairness
E. Operation example
F. Application to imaging device
G. Application to in-vehicle camera
H. Application to medical system

A. Overview

Artificial intelligence includes, for example, a model using a type such as a neural network, support vector regression, or Gaussian process regression. In the present specification, a model of a neural network type will be mainly described, for convenience. However, the present disclosure is not limited to a specific model type, and can be similarly applied to models other than the neural network. Use of artificial intelligence includes a "learning phase" in which learning of a model is performed and an "inference phase" in which inference is performed using a learned model. The inference includes recognition processing such as image recognition and voice recognition, and prediction processing for estimating and predicting an event. The present disclosure is particularly applied to a model for determining classification problems such as image classification.

In the learning phase of the artificial intelligence, a model is learned by a learning algorithm such as error back propagation such that a correct label corresponding to each piece of input data can be outputted, by using a data set including a combination of data (hereinafter, also referred to as "input data") inputted to the model and a label desired to be estimated by the model for the input data. Then, in the inference phase of the artificial intelligence, a model (hereinafter, also referred to as a "learned model") learned in the learning phase outputs an appropriate label for input data.

By performing deep learning using a huge amount of learning data sets, it is possible to obtain artificial intelligence that realizes inference exceeding human ability. However, if there is bias in learning data between categories, there is a possibility that a learning model has bias such that fair determination cannot be made depending on the category.

For example, the unfairness of determination between categories can be corrected by a method of performing model learning by enhancing learning data for a category of a minority attribute for which the number of pieces of data for learning is small and fair determination cannot be made, or a method of reducing learning data for other categories of a majority attribute for which fair determination can be made. However, manually adjusting a large amount of learning data required in deep learning is to be very difficult work. Furthermore, in a case where learning data is related to personal information such as a face image, it is necessary to obtain consent of the person in question in order to acquire the data, which is a high hurdle. In short, enhancing learning data is not realistic. Whereas, reducing the number of pieces of learning data of other categories causes a problem that accuracy of the model for the category is deteriorated.

Therefore, in the present disclosure, learning data of a minority attribute is artificially generated from original learning data. By artificially increasing the learning data of the minority attribute, it is possible to eliminate imbalance of learning data for each attribute and learn a machine learning model such that fair determination without bias can be made. Furthermore, since the additional learning data is increased from already acquired original learning data by calculation processing, work is easier than a case of manual adjustment, and a hurdle for obtaining consent of the person in question or the like is lowered.

For example, additional learning data can be artificially generated from a part or all of learning data for a minority attribute included in the original learning data, by using the Adversarial Example (see, for example, Non Patent Document 1). The Adversarial Example is an image that cannot be perceived by humans but affects machine learning. For example, the Adversarial Example can be easily generated (that is, with a small calculation load), by using a fast gradient sign method (FGSM).

B. Learning System

FIG. 1 illustrates a functional configuration example of a learning system 100 to which the present disclosure is applied. Although the illustrated learning system 100 is used by being installed on, for example, an edge device, some or all of the functions of the learning system 100 may be constructed on a cloud or an arithmetic device capable of large-scale computation. The learning system 100 includes a learning data holding unit 101, a learning unit 102, a model parameter holding unit 103, an analysis unit 104, a data generation unit 105, an inference unit 111, a data input unit 112, and an input data processing unit 113. Note that all the individual functional modules 101 to 105 described above may be arranged in a single device, or may be arranged dispersedly in two or more physically independent devices.

The learning data holding unit 101 accumulates data sets to be used by the learning unit 102 for model learning. In a case where the learning unit 102 performs deep learning, a huge amount of data sets are accumulated in the learning data holding unit 101.

The data set generally includes a combination (x, y) of data x to be inputted to a model as a learning target and a correct answer label y that is a correct answer for the data x. Explanatory variables of the data x include a sensitive attribute that causes a problem such as unfairness of an inference result of a learned model and other non-sensitive attributes. For example, race, gender, age, and the like as the explanatory variables correspond to the sensitive attribute. Among the explanatory variables, in all the present embodiment other than the sensitive attribute, an attribute s of the input data x is further added, and (x, y, s) is treated as the data set. For example, in a case of a data set for image classification, the input data x is a face image of a person, and the attribute s is age, gender, race, ethnicity, and the like of the person.

The learning unit 102 sequentially reads the data set from the learning data holding unit 101, to learn a model. The model is configured by a neural network, for example, but may be a model using a type such as support vector regression or Gaussian process regression. Then, the learning unit 102 stores a model parameter obtained as a learning result, in the model parameter holding unit 103. The model parameter is a variable element that defines the model, and is, for example, a coefficient, a weighting coefficient, or the like to be given to each neuron of the neural network model.

The inference unit 111, the data input unit 112, and the input data processing unit 113 implement the inference phase of the learned model. The data input unit 112 inputs sensor information acquired by a sensor included in the edge device. The input data processing unit 113 performs data processing on data inputted from the data input unit 112 so as to have a data format that can be inputted to a model (for example, the neural network model), and inputs the data to the inference unit 111. The inference unit 111 outputs a label inferred from the input data by using the model in which the model parameter read from the model parameter holding unit 103 is set, that is, a learned model.

The analysis unit 104 analyzes data bias in a data set to be used by the learning unit 102 for model learning, and acquires information regarding bias of the learning data. The data bias means a state in which a data set to be used for learning is concentrated on some attributes, and a data set of a minority attribute and a data set of a majority attribute are generated. The analysis unit 104 may acquire information regarding the data bias in the data set by means other than analysis.

A method for the analysis unit 104 to analyze bias of the learning data set is not particularly limited. The analysis unit 104 may analyze the explanatory variable of a data set accumulated in the learning data holding unit 101, may analyze the explanatory variable of a data set read by the learning unit 102 from the learning data holding unit 101, may analyze the model learned by the learning unit 102, or may analyze fairness of a result of inference by the inference unit 111 using the learned model. Furthermore, the analysis unit 104 may analyze bias of the learning data set on the basis of a method such as explainable AI (XAI), a confidence score calculation of learning data, an influence function calculation, or a Bayesian deep newral network (DNN).

The data generation unit 105 generates learning data found to have a minority attribute from an analysis result obtained by the analysis unit 104, and additionally stores the learning data in the learning data holding unit 101. The analysis unit 104 reads a data set having a corresponding attribute from the learning data holding unit 101, and artificially generates a learning data set having the minority attribute from the read original data set.

Therefore, by artificially increasing the learning data of the minority attribute, the learning system 100 can eliminate imbalance of the learning data for each attribute and learn the machine learning model such that fair determination without bias can be made. Furthermore, since the additional learning data is increased from already acquired original learning data by calculation processing, work is easier than a case of manual adjustment, and a hurdle for obtaining consent of the person in question or the like is lowered.

C. Addition of Learning Data

A model learned using the data set (x, y) can be regarded as a function f for computing an objective variable y from an explanatory variable x (y=f(x)). For example, the explanatory variable is a face image, and the objective variable is person sensing, face identification, or the like. The explanatory variable x(s) is roughly divided into an explanatory variable x(s=0) of a sensitive attribute (s=0) related to unfairness of an objective variable such as race, gender, and age, and all the explanatory variables x(s=1) other than the sensitive attribute (s=1). There is a need for a method of learning a model to make fair determination without bias, without being affected by the explanatory variable x(s=0) related to the sensitive attribute.

Therefore, in the present disclosure, additional learning data is artificially generated from learning data of a minority attribute included in original learning data by using the Adversarial Example, and the learning data is added. According to the present disclosure, since the additional learning data is artificially generated from the original learning data, it is not necessary to supplement actual data, which can be a realistic method.

Figure 2:
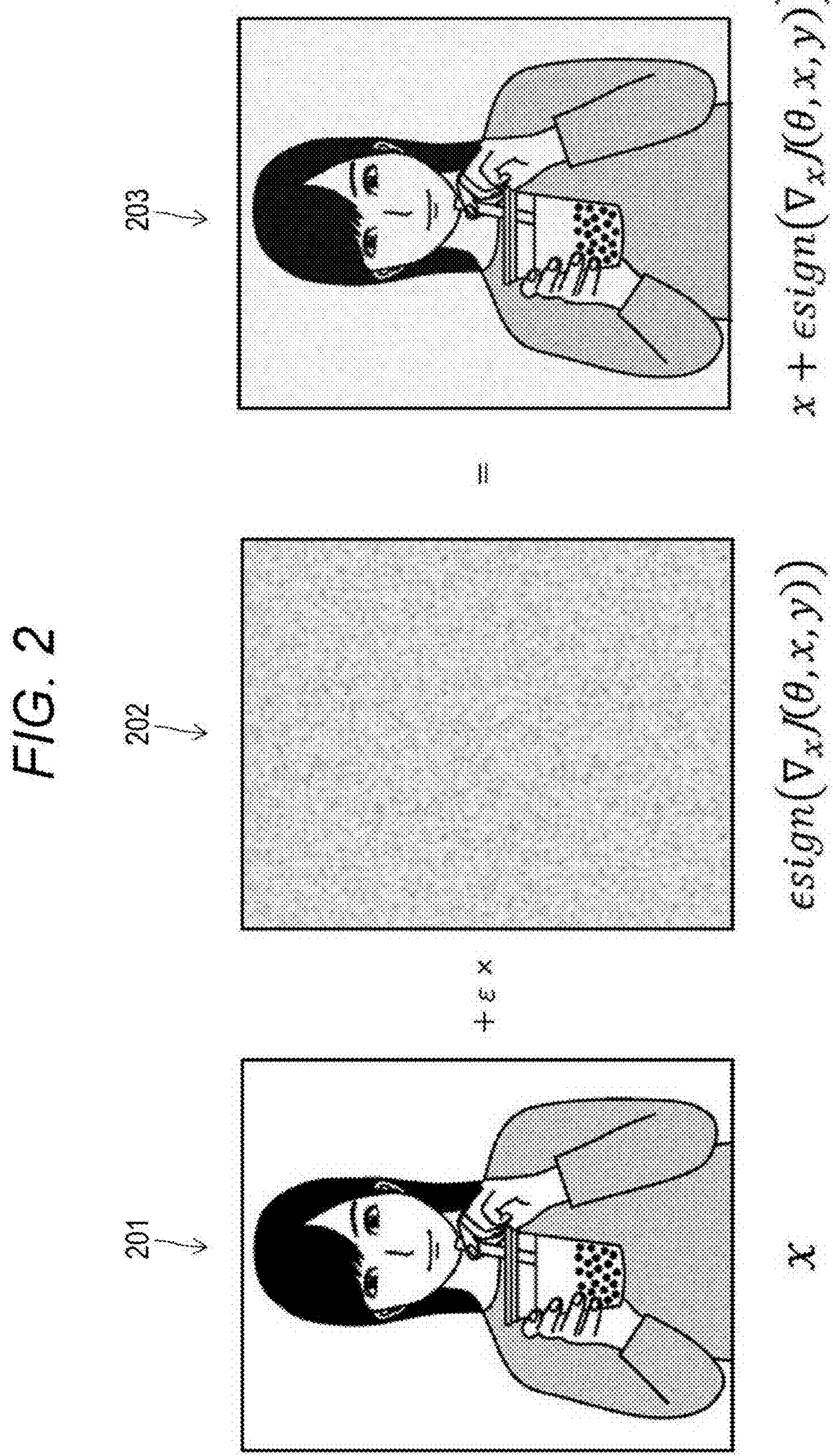
FIG. 2 is a view illustrating a state of generating Adversarial Example.

The Adversarial Example is an image that cannot be perceived by humans but affects machine learning. FIG. 2 illustrates a state in which Adversarial Example 203 is generated by superimposing minute noise 202 on an original image 201. For example, the Adversarial Example can be easily generated by using a fast gradient sign method (FGSM). According to the FGSM, as illustrated in the right side of the following Equation (1), the Adversarial Example on the left side can be generated by an update formula for adding (or subtracting) an appropriate value in a direction in which a loss increases with respect to the original image x.

[Formula 1]

$$\tilde{x}=x+\epsilon\ \mathrm{sign}(\nabla_x J(\theta,x,y)) \tag{1}$$

In the above Equation (1), x is input data (an image vector), y is a correct answer label, is an appropriate small value, J is a loss function, and θ is a model parameter. According to the above Equation (1), the Adversarial Example that increases a loss between with a correct answer label is generated by giving perturbation represented by the second term on the right side to the original data x of the first term on the right side.

$\epsilon(\nabla_x J(\theta, x, y))$ of the second term on the left side of the above Equation (1) is noise that cannot be determined by a human. When the noise of the second term on the left side is added to the original data x of the first term on the left side, a classifier of x erroneously determines as y' instead of y, for example.

In consideration of the attribute s of the data x, a generation formula of the Adversarial Example shown in the above Equation (1) can be expressed as the following Equation (2). However, as shown in the following Equation (3), s in the following Equation (2) takes a value of either s=0 or s=1 depending on the attribute. An attribute of sensitive data (a minority attribute) is set to an attribute value s=0, and an attribute of other non-sensitive data (a majority attribute) is set to an attribute value s=1.

[Formula 2]

$$\tilde{x}(s) = x(s) + \epsilon\mathrm{sign}\left(\nabla_x J(\theta, x, y|x(s))\right) \tag{2}$$

[Formula 3]

$$\text{Sensitive attribute } s \in \{0, 1\} \begin{cases} 0 & \text{Non-protected (Minority attribute)} \\ 1 & \text{Protected (Majority attribute)} \end{cases} \tag{3}$$

Using the above Equation (2), two types of the Adversarial Example of x(s=0) and x(s=1) can be generated from the original data x(s) as shown in the following Equations (4) and (5).

[Formula 4]

$$\tilde{x}(s=0)=x(s=0)+\epsilon\ \mathrm{sign}(\nabla_x J(\theta,x,y|x(s=0))) \tag{4}$$

[Formula 5]

$$\tilde{x}(s=1)=x(s=1)+\epsilon\ \mathrm{sign}(\nabla_x J(\theta,x,y|x(s=1))) \tag{5}$$

Figure 3:
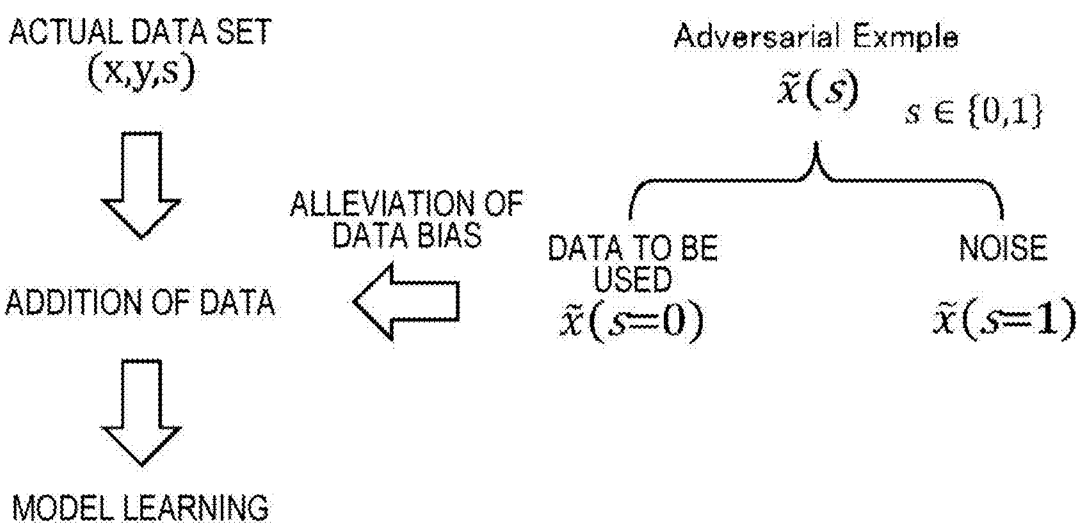
FIG. 3 is a view illustrating a mechanism for adding learning data.

FIG. 3 illustrates a mechanism for adding learning data in the present disclosure. Among the two types of Adversarial Examples that can be generated from the original data x(s), x(s=0) is added to learning data to eliminate data bias, but x(s=1) is not used as noise. Then, a model is learned by using data obtained by adding the Adversarial Example to an original data set. Therefore, according to the present disclosure, by performing learning by adding a data set of a minority attribute, it is possible to learn a fair model that is less likely to be affected by the explanatory variable related to the sensitive attribute.

D. Fairness

Regarding fairness, there is a problem of fairness between groups and between individuals.

Figure 4:
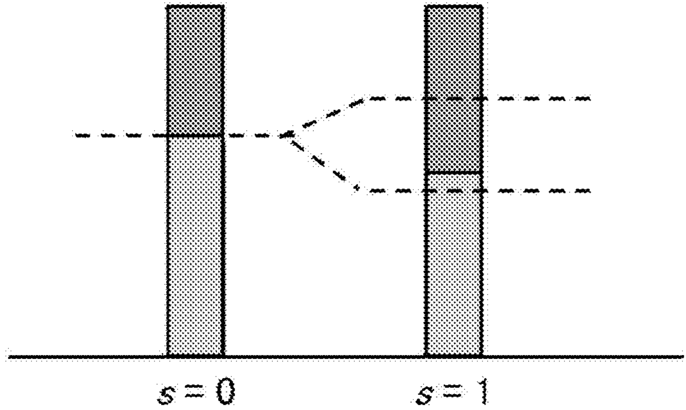
FIG. 4 is a view illustrating a state in which unfairness between groups occurs on the basis of a difference due to a sensitive attribute.

The fairness between groups in the former is caused by a difference due to sensitive attributes of different groups. FIG. 4 illustrates a state in which unfairness between groups occurs on the basis of a difference due to a sensitive attribute. As a solution thereof, control that does not depend on a group is required.

Figure 5:
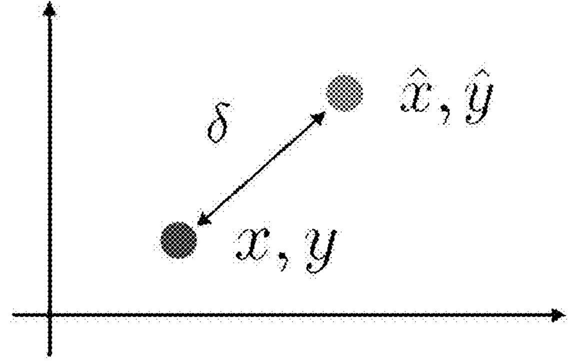
FIG. 5 is a view illustrating a state in which unfairness occurs between individuals.

Whereas, the fairness between individuals in the latter means a case where unfairness between individual persons occurs. FIG. 5 illustrates a state in which unfairness occurs between individuals. There is a case where an unfair difference occurs between individual persons having the same ability, as a result. As a solution, adjustment is made such that no difference occurs in results between individual persons.

The present disclosure is a technology for alleviating data bias in unfairness between groups.

E. Operation Example

Figure 6:
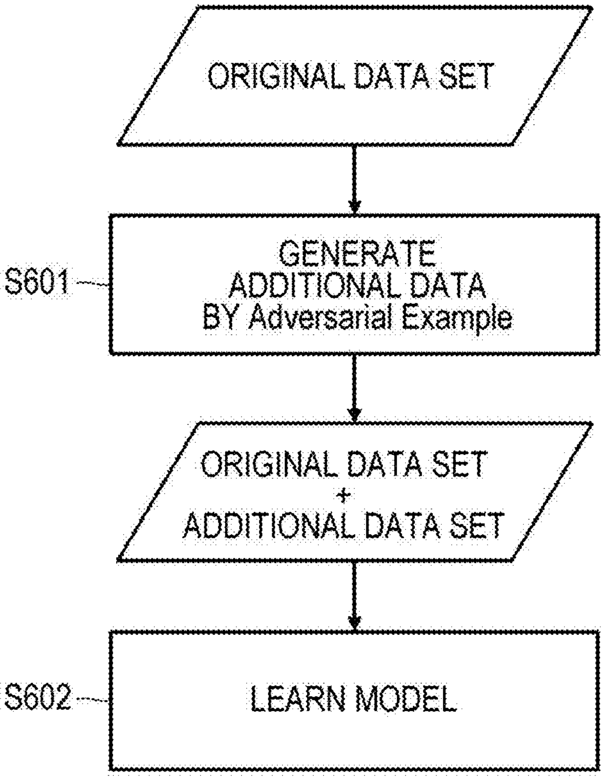
FIG. 6 is a flowchart illustrating an operation example in a learning phase of the learning system 100.

FIG. 6 illustrates an operation example in the learning phase of the learning system 100 illustrated in FIG. 1, in a form of a flowchart.

An original data set stored in the learning data holding unit 101 is inputted to the data generation unit 105. The data generation unit 105 generates additional data according to the above Equation (2) or (4) by the Adversarial Example (step S601). The additional data set including the generated data is stored in the learning data holding unit 101.

Then, the learning unit 102 learns a model by using the original data set and the additional data set stored in the learning data holding unit 101 (step S602). The learning unit 102 stores a model parameter obtained as a learning result, in the model parameter holding unit 103.

In the inference phase, the inference unit 111 outputs a label inferred from data inputted to the data input unit 112, by using the model in which the model parameter read from the model parameter holding unit 103 is set, that is, a learned model.

The data set to be used by the learning unit 102 for learning a model is acquired by purchasing from outside or web crawling. In any of the acquisition routes, the collected data set includes data of a minority attribute, and it is difficult to learn a model while ensuring fairness.

Increasing data of a minority attribute requires collecting the data again, which is practically difficult. Whereas, in a processing procedure illustrated in FIG. 6, the data generation unit 105 generates the Adversarial Example related to data of a minority attribute, and performs learning by adding the Adversarial Example to the data set, so that bias of the original data set can be alleviated.

For example, in a case where the learning system 100 learns a model of person sensing or face identification, it is possible to learn an improved model of person sensing or face identification so as not to make unfair determination for a minority attribute, by adding the Adversarial Example generated from original data to the data set.

FIG. 7 illustrates another operation example in the learning phase of the learning system 100 illustrated in FIG. 1, in a form of a flowchart.

The learning system 100 stands by until an event for which additional data is to be generated occurs (No in step S701). During the standby, the inference unit 111 may perform inference on input data by using a learned model parameter, and output a label.

Here, the event for which additional data is to be generated is not particularly limited. For example, the event may be sensing of a minority attribute by the analysis unit 104 analyzing a data set stored in the learning data holding unit 101. Furthermore, the event may be output of an unfair inference result for input data of a minority attribute by the analysis unit 104 analyzing a learned model. Alternatively, the event may be pointing out of unfairness by a user who looks at an output label of the inference unit 111.

When the event for which additional data is to be generated occurs (Yes in step S701), the analysis unit 104 analyzes an attribute of data to be added (step S702).

The data generation unit 105 reads a data set having an attribute to be added from the learning data holding unit 101 on the basis of an analysis result obtained by the analysis unit 104 (step S703), and generates additional data according to the above Equation (2) or (4) by the Adversarial Example (step S704). The additional data set including the generated data is stored in the learning data holding unit 101.

Then, the learning unit 102 learns a model by using the original data set and the additional data set stored in the learning data holding unit 101 (step S705). The learning unit 102 stores a model parameter obtained as a learning result, in the model parameter holding unit 103.

Also by the processing procedure illustrated in FIG. 7, since the data generation unit 105 generates the Adversarial Example related to data of a minority attribute and adds the Adversarial Example to a data set, bias of the original data set can be alleviated. For example, in a case where the learning system 100 learns a model of person sensing or face identification, it is possible to learn an improved model of person sensing or face identification so as not to make unfair determination for a minority attribute, by adding the Adversarial Example generated from original data to the data set.

F. Application to Imaging Device

Figure 8:
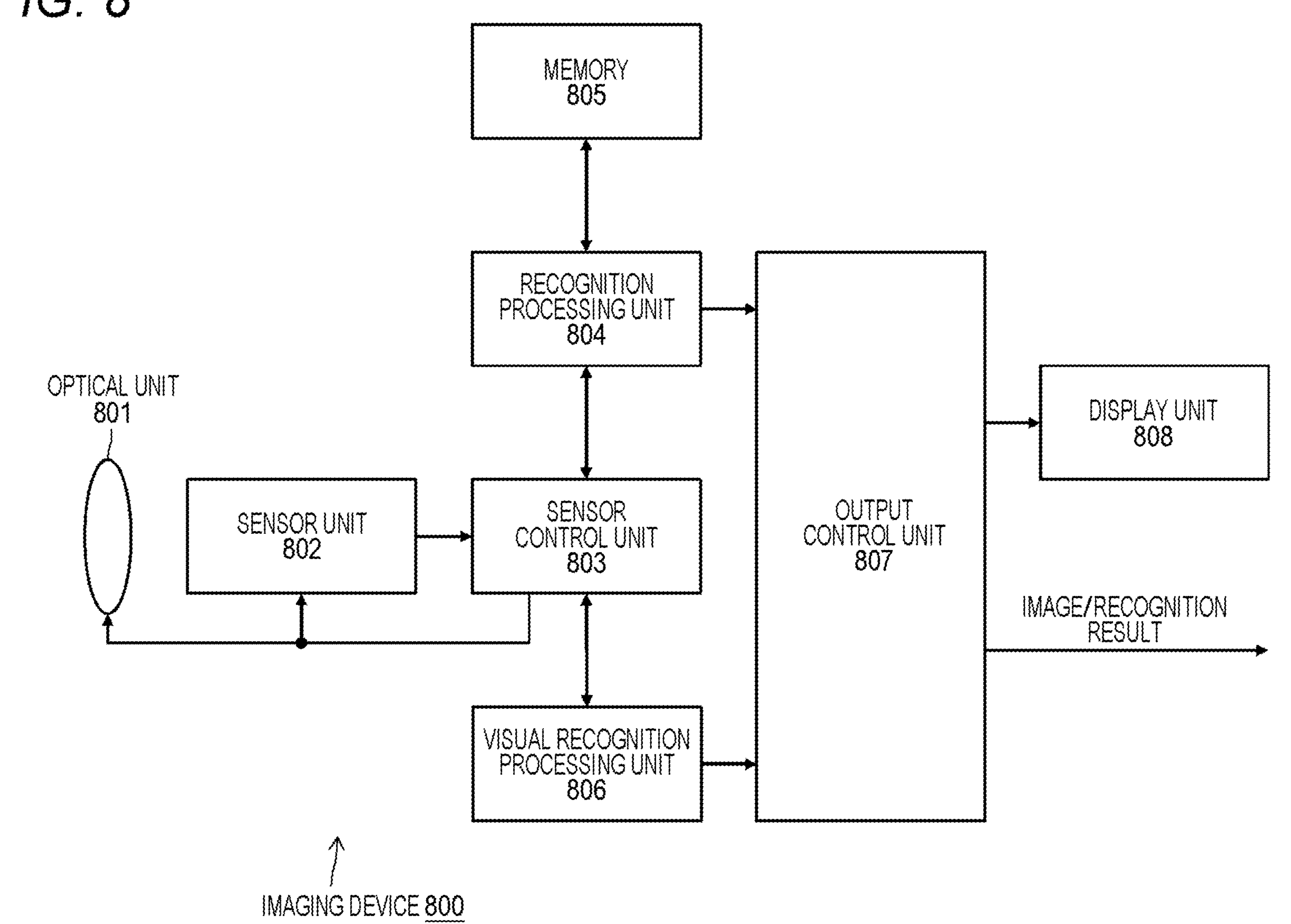
FIG. 8 is a diagram illustrating a functional configuration example of an imaging device 800.

The present disclosure may be applied to a variety of devices that use machine learning models. FIG. 8 illustrates a functional configuration example of an imaging device 800 to which the present disclosure can be applied. The illustrated imaging device 800 includes an optical unit 801, a sensor unit 802, a sensor control unit 803, a recognition processing unit 804, a memory 805, a visual recognition processing unit 806, an output control unit 807, and a display unit 808. For example, a CMOS image sensor can be formed by integrating the sensor unit 802, the sensor control unit 803, the recognition processing unit 804, and the memory 805, by using a complementary metal oxide semiconductor (CMOS). However, the imaging device 800 may be an infrared light sensor that captures an image with infrared light or other type of light sensor.

The optical unit 801 includes, for example, a plurality of optical lenses to condense light from a subject on a light receiving surface of the sensor unit 802, a diaphragm mechanism to adjust a size of an opening with respect to incident light, and a focus mechanism to adjust a focus of irradiation light on the light receiving surface. The optical unit 801 may further include a shutter mechanism that adjusts a time during which the light receiving surface is irradiated with light. The diaphragm mechanism, the focus mechanism, and the shutter mechanism included in the optical unit are configured to be controlled by, for example, the sensor control unit 803. Note that the optical unit 801 may be configured integrally with the imaging device 800 or may be configured separately from the imaging device 800.

The sensor unit 802 includes a pixel array in which a plurality of pixels is arranged in a matrix. Each pixel includes a photoelectric conversion element, and a light receiving surface is formed by individual pixels arranged in a matrix. The optical unit 801 forms an image of incident light on the light receiving surface, and each pixel of the sensor unit 802 individually outputs a pixel signal corresponding to irradiation light. The sensor unit 802 further includes a drive circuit to drive each pixel included in the pixel array, and a signal processing circuit that performs predetermined signal processing on a signal read from each pixel and outputs the signal as a pixel signal of each pixel. The sensor unit 802 outputs a pixel signal of each pixel included in a pixel region, as digital image data.

The sensor control unit 803 includes a microprocessor, for example, controls reading of pixel data from the sensor unit 802, and outputs image data based on each pixel signal read from each pixel. The pixel data outputted from the sensor control unit 803 is passed to the recognition processing unit 804 and the visual recognition processing unit 806.

Furthermore, the sensor control unit 803 generates an imaging control signal for controlling imaging in the sensor unit 802, and supplies the imaging control signal to the sensor unit 802. The imaging control signal includes information indicating exposure and analog gain at the time of imaging in the sensor unit 802. The imaging control signal further includes a control signal for performing an imaging operation of the sensor unit 802, such as a vertical synchronization signal or a horizontal synchronization signal.

The recognition processing unit 804 performs recognition processing (person sensing, face identification, image classification, and the like) of an object included in an image based on pixel data, on the basis of the pixel data passed from the sensor control unit 803. However, the recognition processing unit 804 may perform the recognition processing by using image data after the visual recognition processing by the visual recognition processing unit 806. The recognition result obtained by the recognition processing unit 804 is passed to the output control unit 807.

In the present embodiment, the recognition processing unit 804 performs recognition processing by using a machine learning model. Model parameters obtained by preliminary model learning are stored in the memory 805, and the recognition processing unit 804 performs the recognition processing using a model in which a model parameter read from the memory 805 is set. Furthermore, in a case where the model parameter used by the recognition processing unit 804 cannot ensure fairness of a recognition result for pixel data or image data of a minority attribute, additional learning of the model may be performed using the Adversarial Example generated from existing (or original) data of the minority attribute.

The visual recognition processing unit 806 executes processing for obtaining an image suitable for visual recognition by humans on the pixel data passed from the sensor control unit 803, and outputs image data including a group of pixel data, for example. For example, in a case where a color filter is provided for each pixel included in the sensor unit 802, and each piece of pixel data has color information of any of red (R), green (G), or blue (B), the visual recognition processing unit 806 executes demosaic processing, white balance processing, and the like. Furthermore, the visual recognition processing unit 806 can instruct the sensor control unit 803 to read pixel data necessary for the visual recognition processing from the sensor unit 802. The visual recognition processing unit 806 passes the image data in which the pixel data has been processed, to the output control unit 807. For example, by an image signal processor executing a program stored in advance in a local memory (not illustrated), the above-described function of the visual recognition processing unit 806 is implemented.

The output control unit 807 includes, for example, a microprocessor. To the output control unit 807, a recognition result of an object included in an image is passed from the recognition processing unit 804, and image data as a visual recognition processing result is passed from the visual recognition processing unit 806, and the output control unit 807 outputs one or both of them to outside the imaging device 800. Furthermore, the output control unit 807 outputs the image data to the display unit 808. The user can visually recognize a display image on the display unit 808. The display unit 808 may be built in the imaging device 800 or may be externally connected to the imaging device 800.

Figure 9:
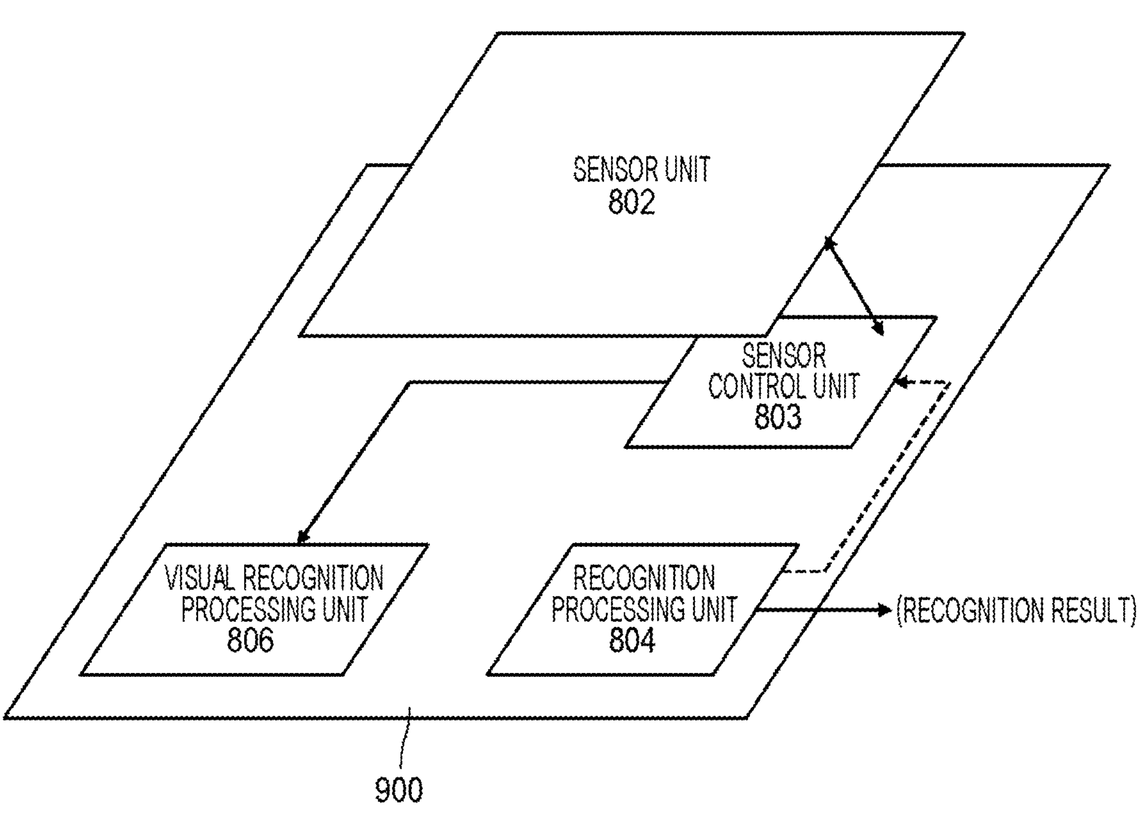
FIG. 9 is a view illustrating a hardware implementation example of the imaging device 800.

FIG. 9 illustrates a hardware implementation example of the imaging device 800. In the example illustrated in FIG. 9, the sensor unit 802, the sensor control unit 803, the recognition processing unit 804, the memory 805, the visual recognition processing unit 806, and the output control unit 807 are mounted on one chip 900. However, in FIG. 9, illustration of the memory 805 and the output control unit 807 is omitted in order to prevent confusion of the drawing.

In the configuration example illustrated in FIG. 9, a recognition result obtained by the recognition processing unit 804 is outputted to outside the chip 900 via the output control unit 807. Furthermore, the recognition processing unit 804 can acquire pixel data or image data to be used for recognition, from the sensor control unit 803 via an interface inside the chip 900.

FIG. 10 illustrates another hardware implementation example of the imaging device 800. In the example illustrated in FIG. 10, the sensor unit 802, the sensor control unit 803, the visual recognition processing unit 806, and the output control unit 807 are mounted on one chip 1000, but the recognition processing unit 804 and the memory 805 are arranged outside the chip 1000. However, also in FIG. 10, illustration of the memory 805 and the output control unit 807 is omitted in order to prevent confusion of the drawing.

In the configuration example illustrated in FIG. 10, the recognition processing unit 804 acquires pixel data or image data to be used for recognition, from the output control unit 807 via a communication interface between chips. Furthermore, the recognition processing unit 804 directly outputs the recognition result to outside. Of course, a configuration may be adopted in which the recognition result obtained by the recognition processing unit 804 is returned to the output control unit 807 in the chip 1000 via a communication interface between chips, and is outputted from the output control unit 807 to outside the chip 1000.

In the configuration example illustrated in FIG. 9, since both the recognition processing unit 804 and the sensor control unit 803 are mounted on the same chip 900, communication between the recognition processing unit 804 and the sensor control unit 803 can be executed at high speed via the interface in the chip 900. Whereas, in the configuration example illustrated in FIG. 10, since the recognition processing unit 804 is arranged outside the chip 1000, replacement of the recognition processing unit 804 is easy, and a learning model can be exchanged by replacement. However, it is necessary to perform communication between the recognition processing unit 804 and the sensor control unit 803 via an interface between chips, which lowers the speed.

Figure 11:
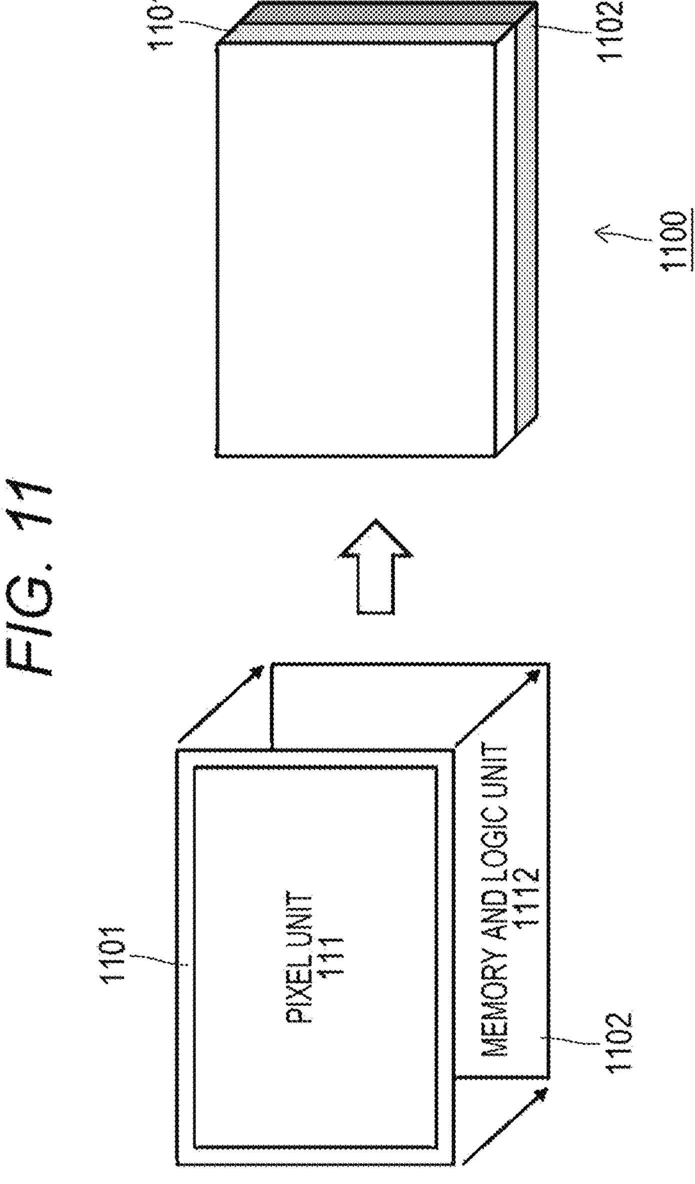
FIG. 11 is a view illustrating an example in which a semiconductor chip of the imaging device 800 is formed as a stacked image sensor 1100 having a two-layer structure.

FIG. 11 illustrates an example in which the semiconductor chip 900 (or 1000) of the imaging device 800 is formed as a stacked image sensor 1100 having a two-layer structure in which two layers are stacked. In the illustrated structure, a pixel unit 1111 is formed in a semiconductor chip 1101 of a first layer, and a memory and logic unit 1112 is formed in a semiconductor chip 1102 of a second layer.

The pixel unit 1111 includes at least a pixel array in the sensor unit 802. Furthermore, the memory and logic unit 1112 includes, for example, the sensor control unit 803, the recognition processing unit 804, the memory 805, the visual recognition processing unit 806, the output control unit 807, and an interface that performs communication between the imaging device 800 and outside. The memory and logic unit 1112 further includes a part or all of a drive circuit that drives the pixel array in the sensor unit 802. Furthermore, although not illustrated in FIG. 11, the memory and logic unit 1112 may further include, for example, a memory used by the visual recognition processing unit 806 for processing image data.

As illustrated on the right side of FIG. 11, the imaging device 800 is configured as one solid-state imaging element by bonding the semiconductor chip 1101 of the first layer and the semiconductor chip 1102 of the second layer while electrically contacting each other.

Figure 12:
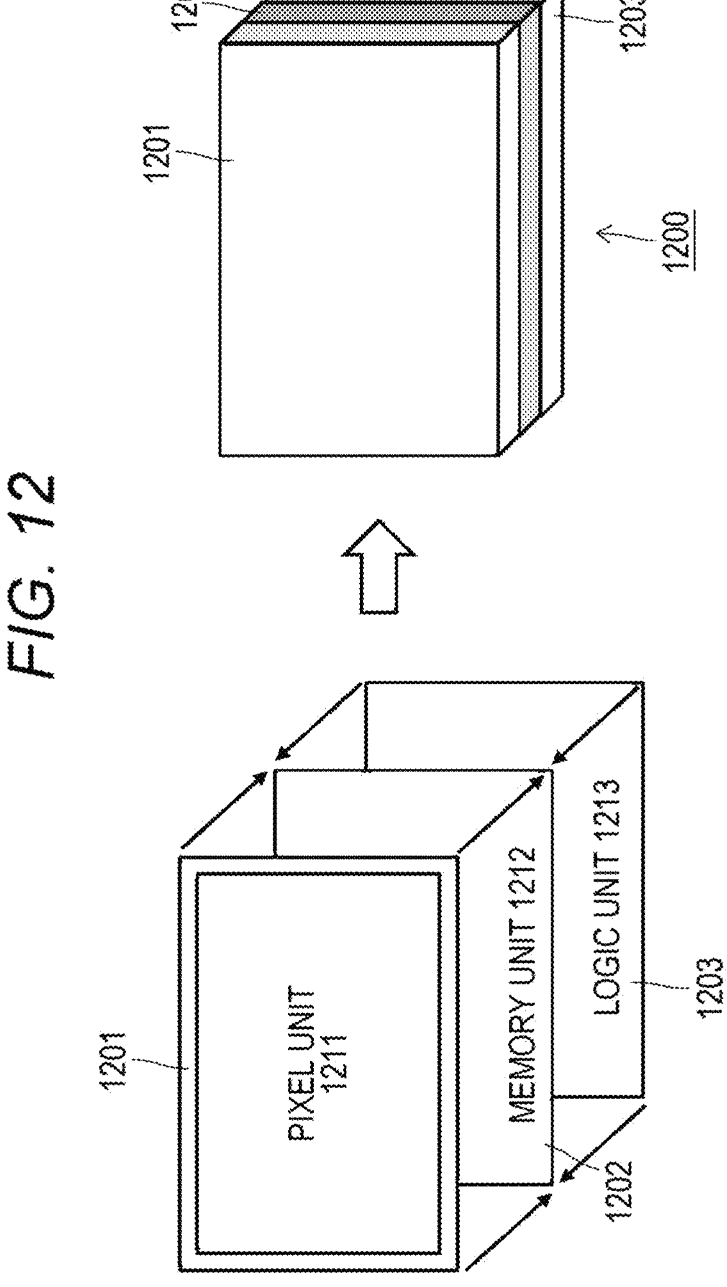
FIG. 12 is a view illustrating an example in which a semiconductor chip of the imaging device 800 is formed as a stacked image sensor 1200 having a three-layer structure.

FIG. 12 illustrates an example in which the semiconductor chip 900 (or 1000) of the imaging device 800 is formed as a stacked image sensor 1200 having a two-layer structure in which three layers are stacked. In the illustrated structure, a pixel unit 1211 is formed in a semiconductor chip 1201 of a first layer, a memory unit 1212 is formed in a semiconductor chip 1202 of a second layer, and a logic unit 1213 is formed in a semiconductor chip 1203 of a third layer.

The pixel unit 1211 includes at least a pixel array in the sensor unit 802. Furthermore, the logic unit 1213 includes, for example, the sensor control unit 803, the recognition processing unit 804, the visual recognition processing unit 806, the output control unit 807, and an interface that performs communication between the imaging device 800 and outside. The logic unit 1213 further includes a part or all of a drive circuit that drives the pixel array in the sensor unit 802. Furthermore, in addition to the memory 805, the memory unit 1212 may further include, for example, a memory used by the visual recognition processing unit 806 for processing image data.

As illustrated on a right side of FIG. 12, the imaging device 800 is configured as one solid-state imaging element by bonding the semiconductor chip 1201 of the first layer, the semiconductor chip 1202 of the second layer, and the third semiconductor chip 1203 while electrically contacting each other.

Figure 13:
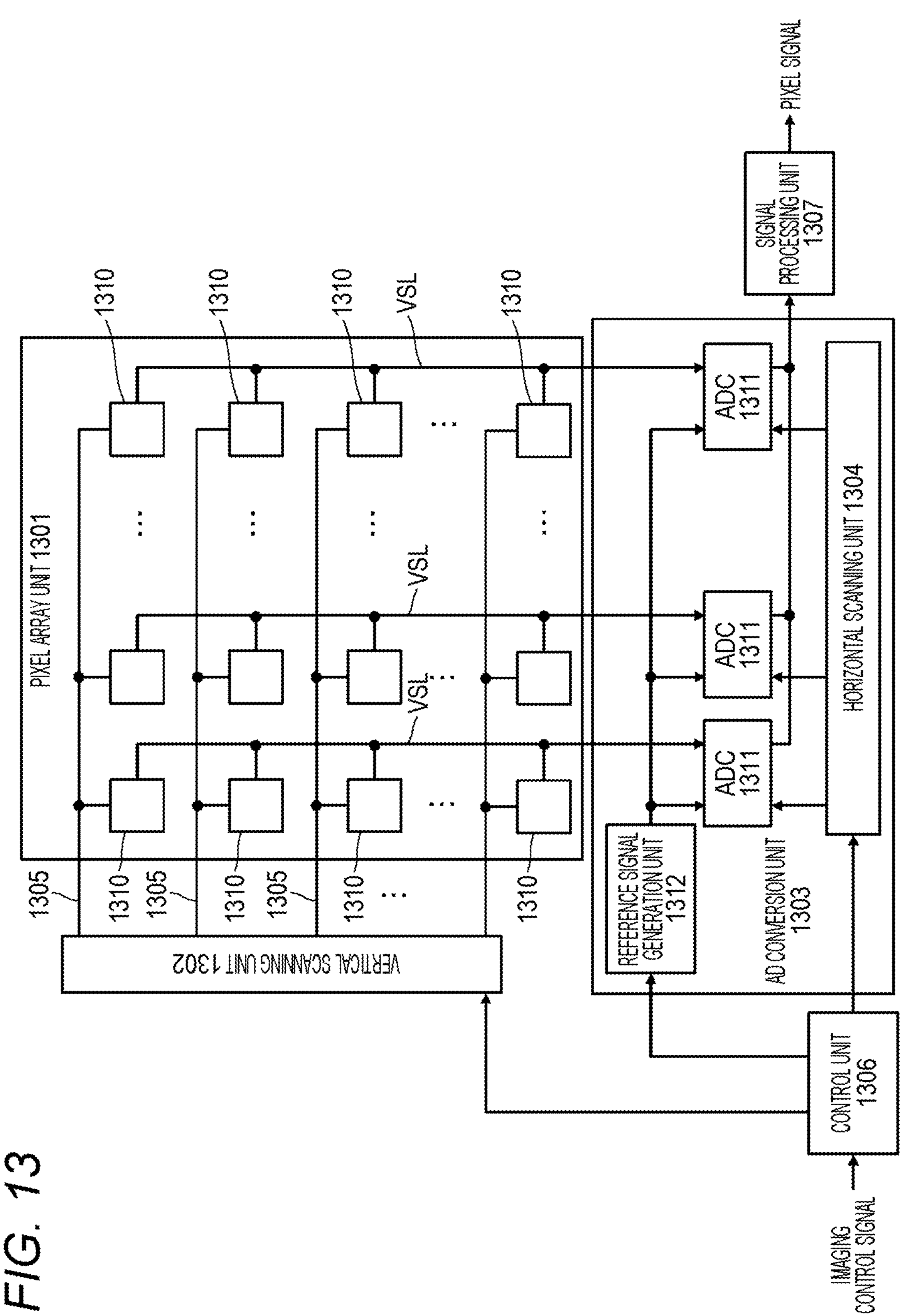
FIG. 13 is a diagram illustrating a configuration example of a sensor unit 802.

FIG. 13 illustrates a configuration example of the sensor unit 802. The illustrated sensor unit 802 includes a pixel array unit 1301, a vertical scanning unit 1302, an analog to digital (AD) conversion unit 1303, a horizontal scanning unit 1304, a pixel signal line 1305, a vertical signal line VSL, a control unit 1306, and a signal processing unit 1307. Note that the control unit 1306 and the signal processing unit 1307 in FIG. 13 may be included in the sensor control unit 803 in FIG. 8, for example.

The pixel array unit 1301 includes a plurality of pixel circuits 1310 each including a photoelectric conversion element that performs photoelectric conversion on received light and a circuit that reads electric charge from the photoelectric conversion element. The plurality of pixel circuits 1310 is arranged in a matrix in a horizontal direction (a row direction) and a vertical direction (a column direction). The arrangement of the pixel circuits 1310 in the row direction is a line. For example, in a case where an image of one frame is formed with 1920 pixels×1080 lines, the pixel array unit 1301 forms an image of one frame by pixel signals obtained by reading 1080 lines each including 1920 pieces of the pixel circuit 1310.

In the pixel array unit 1301, the pixel signal line 1305 is connected to each row and the vertical signal line VSL is connected to each column, for the row and the column of each pixel circuit 1310. An end portion of each pixel signal 1305 not connected to the pixel array unit 1301 is connected to the vertical scanning unit 1302. Under the control of the control unit 1306, the vertical scanning unit 1302 transmits a control signal such as a drive pulse at the time of reading a pixel signal from a pixel, to the pixel array unit 1301 via the pixel signal line 1305. An end portion of the vertical signal line VSL not connected to the pixel array unit 1301 is connected to the AD conversion unit 1303. The pixel signal read from the pixel is transmitted to the AD conversion unit 1303 via the vertical scanning line VSL.

Reading of the pixel signal from the pixel circuit 1310 is performed by transferring electric charge accumulated in the photoelectric conversion element by exposure to a floating diffusion (FD) layer, and converting the electric charge transferred in the floating diffusion layer into a voltage. A voltage converted from the electric charge in the floating diffusion layer is outputted to the vertical signal line VSL via an amplifier.

The AD conversion unit 1303 includes a column AD converter (ADC) 1311 provided for each vertical signal line VSL, a reference signal generation unit 1312, and the horizontal scanning unit 1304. The column AD converter 1311 is a column AD converter that performs AD conversion processing on each column of the pixel array unit 1301, and the column AD converter 1311 performs AD conversion processing on a pixel signal supplied from the pixel circuit 1310 via the vertical signal line VSL to generate two digital values for correlated double sampling (CDS) processing for performing noise reduction, and outputs the digital values to the signal processing unit 1307.

The reference signal generation unit 1312 generates, as a reference signal, a ramp signal to be used by each column AD converter 1311 to convert a pixel signal into two digital values on the basis of a control signal from the control unit 1306, and supplies the ramp signal to each column AD converter 1311. The ramp signal is a signal in which a voltage level decreases at a constant slope with respect to time, or a signal in which the voltage level decreases stepwise.

Inside the column AD converter 1311, counting is started according to a clock signal by a counter when the ramp signal is supplied, and a pixel signal that is an analog signal is converted into a digital value by comparing a voltage of the pixel signal supplied from the vertical signal line VSL with a voltage of the ramp signal, stopping counting by the counter at a timing when the voltage of the ramp signal exceeds the voltage of the pixel signal, and outputting a value corresponding to a count value at that time.

The signal processing unit 1307 performs CDS processing on the basis of the two digital values generated by the column AD converter 1311, generates a pixel signal (pixel data) of a digital signal, and outputs the pixel signal to outside the sensor control unit 803.

The horizontal scanning unit 1304 sequentially outputs digital values temporarily held by the individual column AD converters 1311 to the signal processing unit 1307, by performing a selection operation to select the individual column AD converters 1311 in a predetermined order under the control of the control unit 1306. The horizontal scanning unit 1304 is configured using, for example, a shift register, an address decoder, and the like.

The control unit 1306 generates a drive signal for controlling driving of the vertical scanning unit 1302, the AD conversion unit 1303, the reference signal generation unit 1312, the horizontal scanning unit 1304, and the like on the basis of an imaging control signal supplied from the sensor control unit 803, and outputs the drive signal to each unit. For example, the control unit 1306 generates a control signal for the vertical scanning unit 1302 to supply to each pixel circuit 1310 via the pixel signal line 1305 on the basis of a vertical synchronization signal and a horizontal synchronization signal included in the imaging control signal, and supplies the control signal to the vertical scanning unit 1302. Furthermore, the control unit 1306 passes information indicating analog gain included in the imaging control signal, to the AD conversion unit 1303. In the AD conversion unit 1303, gain of a pixel signal inputted to each column AD converter 1311 via the vertical signal line VSL is controlled on the basis of the information indicating the analog gain.

On the basis of the control signal supplied from the control unit 1306, the vertical scanning unit 1302 supplies various signals including a drive pulse in the pixel signal line 1305 of the selected pixel industry of the pixel array unit 1301 to each pixel circuit 1310 for each line, and controls to output the pixel signal from each pixel circuit 1310 to the vertical signal line VSL. The vertical scanning unit 1302 is configured using, for example, a shift register, an address decoder, and the like. Furthermore, the vertical scanning unit 1302 controls exposure in each pixel circuit 1310 on the basis of information indicating exposure and supplied from the control unit 1306.

The sensor unit 802 configured as illustrated in FIG. 13 is a column AD type image sensor in which each column AD converter 1311 is arranged for each column.

With reference to FIGS. 8 to 13, a configuration of the imaging device 800 with an image recognition function has been described. In a case where the imaging device 800 is applied to an image classification service, for example, a model used by the recognition processing unit 804 is learned in advance by using a learning data set. Here, it is assumed that sufficient learning cannot be performed for data of a minority attribute included in the original data set, and a recognition rate is lower than that of data of other attributes. Whereas, in the present disclosure, bias of the original data set can be alleviated by generating the Adversarial Example related to data of a minority attribute and performing learning by adding the Adversarial Example to the data set.

Figure 14:
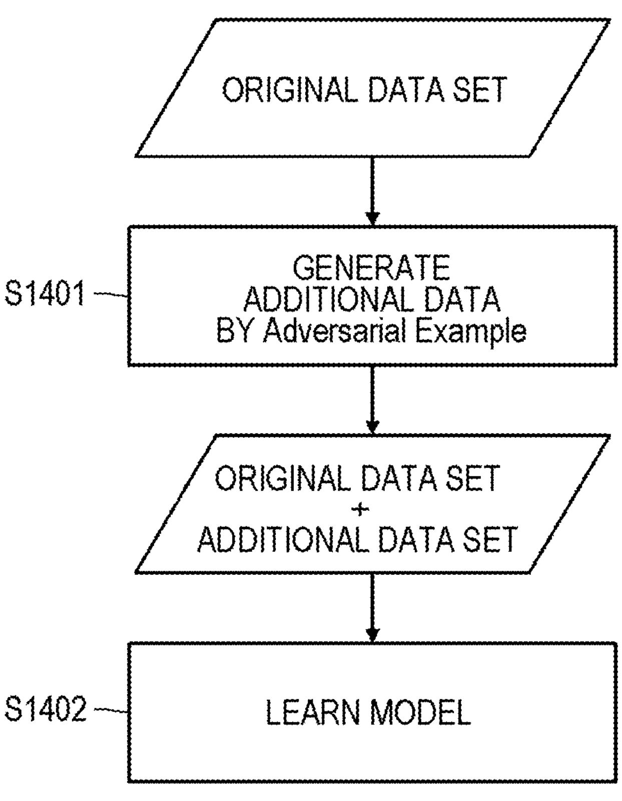
FIG. 14 is a flowchart illustrating an operation example in a learning phase of the imaging device 800 with a recognition function.

FIG. 14 illustrates an operation example in the learning phase for applying the imaging device 800 with a recognition function to an image classification service, in a form of a flowchart.

First, an original data set is inputted, and additional data is generated according to the above Equation (2) or (4) for data of a minority attribute by the Adversarial Example (step S1401).

Then, the recognition processing unit 804 learns a model by using the original data set and the additional data set (step S1402). The model learned in this way can also improve a recognition rate for a minority attribute, and perform image classification while securing fairness.

G. Application to In-Vehicle Camera

When driving a vehicle, it is necessary to sense various objects such as surrounding vehicles, pedestrians, and lanes. For this reason, a technology has been developed in which an object recognition function is mounted on an in-vehicle camera, a driver is notified of a recognition result, and a vehicle is controlled on the basis of the recognition result (see, for example, Patent Document 2).

Figure 15:
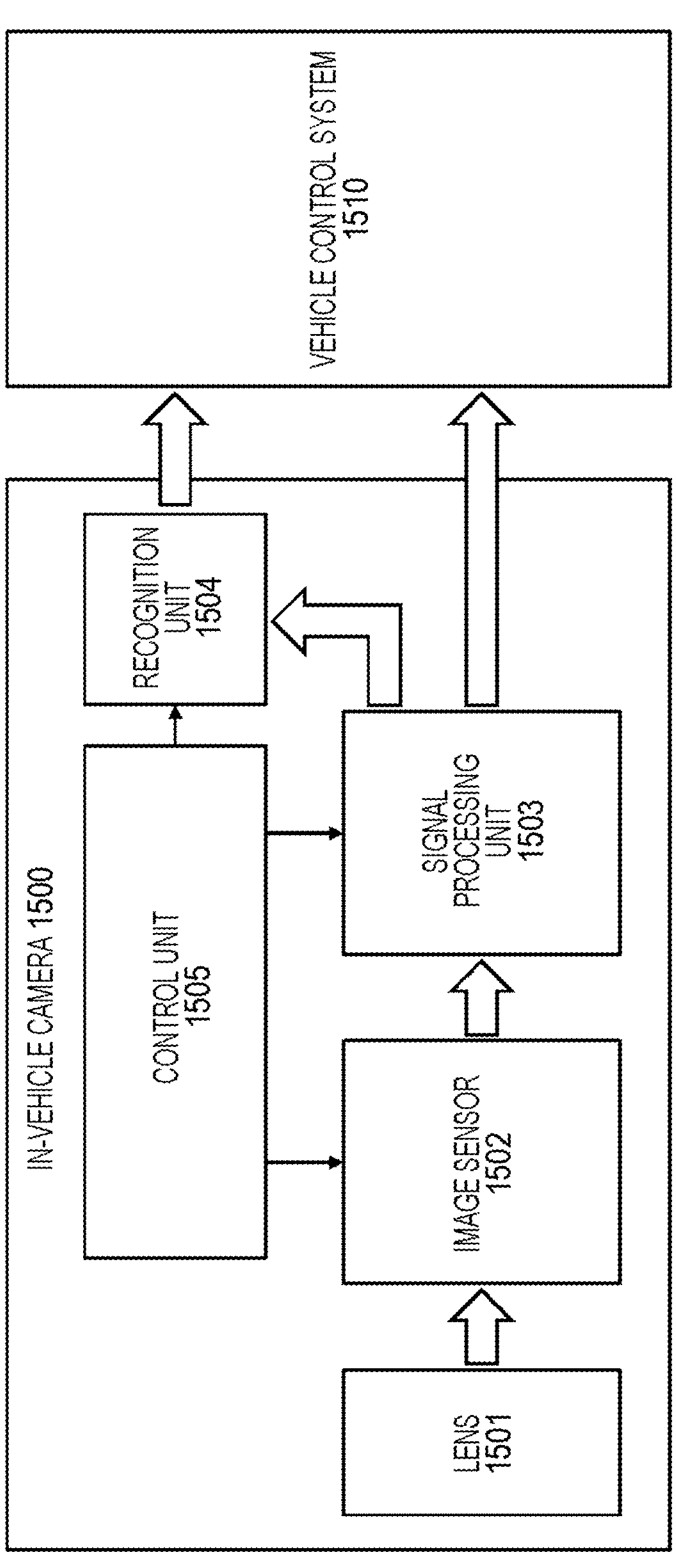
FIG. 15 is a diagram illustrating a functional configuration example of an in-vehicle camera 1500.

FIG. 15 schematically illustrates a functional configuration example of an in-vehicle camera 1500. The illustrated in-vehicle camera 1500 includes a lens 1501, an image sensor 1502, a signal processing unit 1503, a recognition unit 1504, and a control unit 1505.

The image sensor 1502 includes, for example, an element such as a CMOS, and captures an image formed on an imaging surface by the lens 1501. The signal processing unit 1503 performs signal processing on RAW data outputted from the image sensor 1502. The signal processing performed in the signal processing 1503 corresponds to, for example, demosaicing, noise reduction, white balance adjustment, gamma correction, sensor spectral correction, YC conversion, and the like.

The recognition unit 1504 recognizes an object included in a captured image processed by the signal processing unit 1503. The recognition unit 1504 recognizes various objects such as, for example, a motorcycle, a bicycle, a pedestrian, a road sign, a traffic light, a lane, a median strip, a guardrail, a street tree, and a street lamp. The recognition unit 1504 performs object recognition processing by using a learned model configured by a neural network or the like.

The control unit 1505 integrally controls an operation of each unit in the in-vehicle camera 1500. The control unit 1505 controls, for example, an imaging operation in the image sensor 1502 and signal processing in the signal processing unit 1503. Furthermore, the control unit 1505 may add, delete, or change an object to be recognized by the recognition unit 1504.

A vehicle control system 1510 in the subsequent stage controls an operation of an own vehicle, on the basis of an image captured by the image sensor 1502 and developed by the signal processing unit 1503 under the control of the control unit 1505 and on the basis of a recognition result obtained by the recognition unit 1504. The vehicle control described herein includes vehicle control for automated driving or ADAS such as, for example, adaptive cruise control (ACC), lane departure warning (LDW), lane keeping assist (LKA), automatic emergency braking (AEB), and blind spot detection (BSD), and further includes drive control of each drive unit such as an active cornering light (ACL), a brake actuator (BRK), and a steering device (STR).

Figure 16:
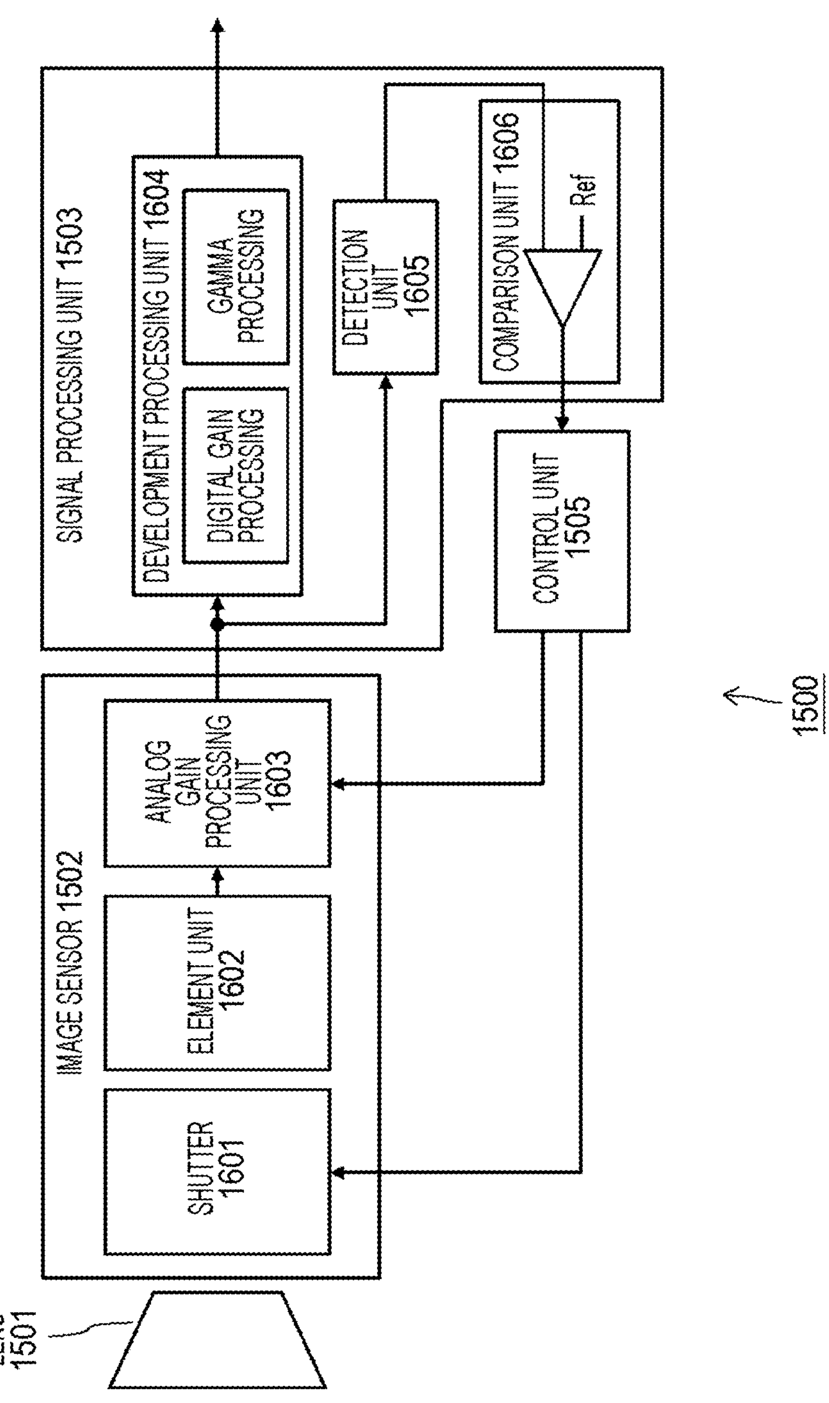
FIG. 16 is a diagram illustrating an internal configuration example of an image sensor 1502 and a signal processing unit 1503.

FIG. 16 illustrates an internal configuration example of the image sensor 1502 and the signal processing unit 1503.

The image sensor 1502 includes a shutter 1601, an element unit 1602, and an analog gain processing unit 1603. Light condensed by the lens 1501 passes through the shutter 1601 and reaches an imaging surface of the element unit 1602. The element unit 1602 includes a two-dimensional pixel array, and a pixel signal corresponding to an amount of received light is outputted from each pixel. Each pixel signal is subjected to amplification processing in an analog region by the analog gain processing unit 1603, is then digitally converted, and is outputted to the signal processing unit 1603.

The signal processing unit 1603 includes a development processing unit 1604, a detection unit 1605, and a comparison unit 1606. The development processing unit 1604 performs development processing including digital gain processing and gamma processing, on a digital pixel signal outputted from the image sensor 1502. Furthermore, the detection unit 1605 senses brightness (luminance) of a screen by performing detection with optical detection (OPD) on the entire screen captured by the image sensor 1502. Then, the comparison unit 1606 compares the brightness of the entire screen sensed by the detection unit 1605 with a predetermined reference value (Ref).

On the basis of a difference between the brightness of the screen outputted from the comparison unit 1606 and the reference value, the control unit 1505 performs control such that an image captured by the image sensor 1502 has appropriate brightness, by controlling an opening/closing timing (that is, an exposure time) of the shutter 1601, adjusting analog gain of the analog gain processing unit 303, and/or adjusting digital gain or other development parameters in the development processing unit 1604.

Note that the in-vehicle camera 1500 is not necessarily intended to capture an image observed by a user (a driver or the like), but is mainly intended to acquire image information that can be used in the vehicle control system 1510 in the subsequent stage. Therefore, development processing performed by the signal processing unit 1503 of the in-vehicle camera 1500 does not need to be the same as that of the imaging device 800.

The in-vehicle camera 1500 has an object recognition function, and recognizes various objects such as, for example, a motorcycle, a bicycle, a pedestrian, a road sign, a traffic light, a lane, a median strip, a guardrail, a street tree, and a street lamp. A model used in the recognition unit 1504 is learned in advance by using a learning data set. Here, it is assumed that sufficient learning cannot be performed for data of a minority attribute included in the original data set, and a recognition rate is lower than that of data of other attributes. For example, a model used in the recognition unit 1504 is learned to recognize a human, but there is imbalance in a data amount between images of a child and an adult, and it is assumed that a recognition rate for a child with a small number of pieces of learning data is low. Whereas, in the present disclosure, an image recognized as a child by the model used in the recognition unit 1504 is generated by the Adversarial Example, and the image is added to perform the image, which makes it possible to learn a model with an improved recognition rate for a child.

Figure 17:
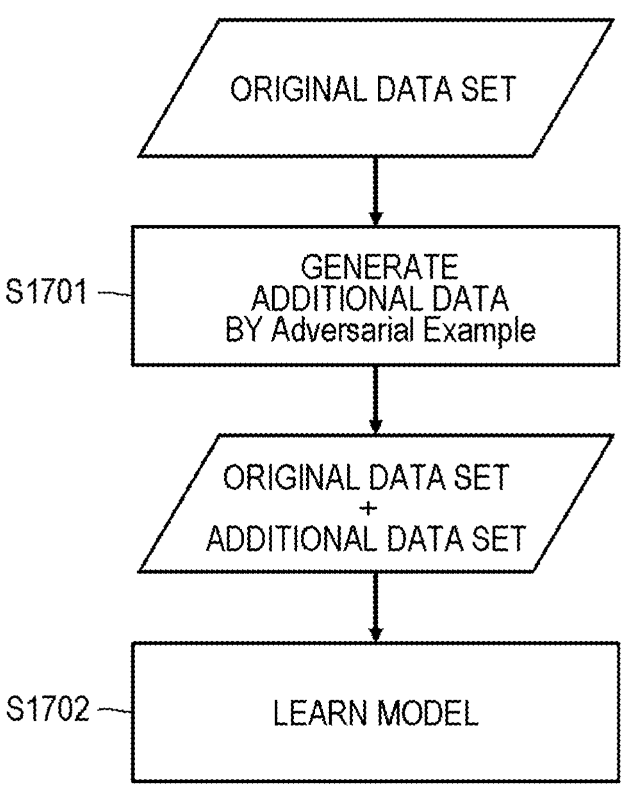
FIG. 17 is a flowchart illustrating an operation example in a learning phase of a recognition unit 1504 of the in-vehicle camera 1500.

FIG. 17 illustrates an operation example for training to recognize a human in the learning phase of the recognition unit 1504 of the in-vehicle camera 1500, in a form of a flowchart.

First, an original data set is inputted, and additional data is generated for an image of a child with a small number of samples according to the above Equation (2) or (4) by the Adversarial Example (step S1701).

Then, the recognition unit 1504 learns a model by using the original data set and the additional data set (step S1702). The model learned in this way can also improve a recognition rate for an image of a child, and can perform recognition while securing fairness for humans in general.

H. Application to Medical System

It is highly expected to utilize artificial intelligence also in a medical field. For example, a learned model can perform recognition processing on endoscopic images to assist in surgery. On the basis of a recognition result obtained by the learned model, a surgeon can appropriately progress the surgery and control an operation of a surgical robot.

FIG. 18 illustrates a configuration example of a medical robot device 1800 using a robot arm. The medical robot device 1800 includes a robot arm 1810 and a control device 1820 that controls an operation of the robot arm 1810.

The robot arm 1810 includes one or a plurality of robot arms including a multi-link structure in which a plurality of links is connected by a joint shaft. In FIG. 18, only one robot arm is illustrated for simplification of the drawing. At a distal end of the robot arm, a medical surgical tool such as an endoscope, forceps, a pneumoperitoneum tube, an energy treatment instrument, tweezers, or a retractor is mounted.

The control device 1820 includes an image recognizer 1821 and a motion predictor 1822. The image recognizer 1821 performs image recognition on a captured image obtained by an endoscope. Furthermore, the motion predictor 1822 predicts a motion of the robot arm of the robot arm 1810 according to a recognition result of the image recognizer 1821.

To the control device 1820, a captured image of a surgical site obtained by the endoscope, and motion information of the robot arm and sensor information of the robot arm from the robot arm 1810 are inputted. The motion information of the robot arm includes information regarding a position, a speed, and an acceleration of a medical instrument such as the endoscope supported at the distal end by the robot arm, and an orientation of each joint of the robot arm (a joint angle measured by an encoder installed on a rotation axis of the joint). Furthermore, the sensor information of the robot arm includes information such as an acceleration measured by an inertial measurement unit (IMU) mounted on the robot arm 1810, information about torque acting on each joint, and information such as an external force acting on a medical instrument supported at the distal end of the robot arm.

The image recognizer 1821 performs image recognition of a medical instrument included in a captured image of the endoscope and an environment in a visual field of the endoscope by using a model learned to perform image recognition, and outputs instrument recognition information and environment recognition information. In the present embodiment, the image recognizer 1821 performs user-specific model learning in practice by using a captured image of the endoscope, and further performs image recognition specialized for user's needs by using a learned model.

The image recognizer 1821 recognizes a type of the medical instrument (for example, forceps, a pneumoperitoneum tube, an energy treatment instrument, tweezers, retractor, and the like), a position and an orientation of each instrument, and an operation state (for example, in the case of forceps, an open/closed state is obtained, and in the case of an energy treatment instrument, an energy output state is obtained) recognized in the field of view of the endoscope as the instrument recognition information. Furthermore, the image recognizer 1821 recognizes, as the environment recognition information, depth information of an organ or a medical instrument included in the captured image in the field of view of the endoscope (including a shape of the organ or the instrument), an environment map in a surgical site (for example, environment map creation using simultaneous localization and mapping (SLAM) technology), a type of the organ, a type of the medical instrument, a material of each object included in the captured image, and the like. Furthermore, the image recognizer 1821 recognizes, for example, each object such as an organ or a medical instrument included in the image of the surgical site and a material thereof, depth information of each object, and an environment map as the environment recognition information.

The motion predictor 1822 predicts target command-related information for the robot arm 1810 on the basis of recognition information such as the instrument recognition information and the environment recognition information by using a model learned to predict a motion of the robot arm from the image recognition result, and outputs the target command-related information. The motion predictor 1822 predicts various target command values such as a camera target position, orientation, speed, acceleration, gaze point, line-of-sight vector (a target object position, distance, vector orientation) of the endoscope, an electronic cut-out position of a captured image, and a distance, for example, as the target command-related information. Furthermore, the motion predictor 1822 predicts a target position, orientation, speed, acceleration, and operation force of the instrument as the target command-related information. Then, the control device 1820 calculates a target joint angle, joint angular velocity, and joint angular acceleration of each joint of the robot arm by inverse kinematics calculation on the basis of the information about the target position, orientation, speed, and acceleration of the medical instrument supported at the distal end of the robot arm such as the endoscope predicted by the motion predictor 1822, and outputs a command value to the robot arm 1810.

A model used in the image recognizer 1821 is learned in advance by using a learning data set such that instrument information and environmental information can be recognized from the endoscopic image. Here, it is assumed that sufficient learning cannot be performed for data of a minority attribute included in the original data set, and a recognition rate is lower than that of data of other attributes. For example, many images of success examples are provided as learning data, but images of failure examples are few. Whereas, in the present disclosure, an image recognized as a failure example by the image recognizer 1821 is generated by the Adversarial Example, and the image is added to perform the image, which makes it possible to learn the model with improved recognition accuracy.

Figure 19:
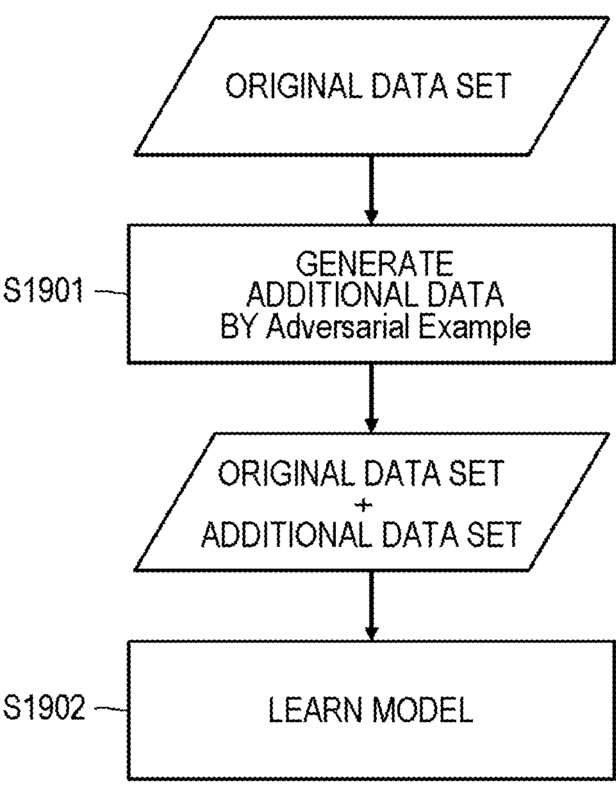
FIG. 19 is a flowchart illustrating an operation example in a learning phase of an image recognizer 1821.

FIG. 19 illustrates an operation example for training to recognize an endoscopic image in the learning phase of the image recognizer 1821, in a form of a flowchart.

First, an original data set is inputted, and additional data is generated for an image of a failure example with a small number of samples according to the above Equation (2) or (4) by the Adversarial Example (step S1901).

Then, the image recognizer 1821 learns a model by using the original data set and the additional data set (step S1902). The model learned in this manner can also improve a recognition rate for an image of a failure example, and can perform recognition while securing fairness for endoscopic images in general.

INDUSTRIAL APPLICABILITY

The present disclosure is heretofore described in detail with reference to the specific embodiment. However, it is obvious that those skilled in the art can make modifications and substitutions of the embodiment without departing from the gist of the present disclosure.

The present disclosure can be mainly applied to learning of a machine learning model for performing image classification, and the machine learning model to which the present disclosure is applied can be installed on, for example, an imaging device. For example, the machine learning model to which the present disclosure is applied can be used for a recognizer of an in-vehicle camera, image recognition of a surgical site in the medical field, and the like.

In short, the present disclosure has been described in an illustrative manner, and the contents described in the present specification should not be interpreted in a limited manner. In order to determine the gist of the present disclosure, the claims should be taken into consideration.

Note that the present disclosure can have the following configurations.

(1) An information processing apparatus including:

an acquisition unit configured to acquire information regarding bias of learning data to be used for learning of a model;

a generation unit configured to generate additional learning data from data included in the learning data on the basis of the information regarding bias; and a learning unit configured to learn the model by using the learning data and the additional learning data.

(2) The information processing apparatus according to (1) described above, in which the acquisition unit acquires information indicating a minority attribute in the first learning data, and from data of the minority attribute included in the first learning data, the data generation unit generates second learning data of a same attribute.

(3) The information processing apparatus according to any one of (1) and (2) described above, in which from data of the minority attribute included in the learning data, the data generation unit generates Adversarial Example to be second learning data.

(4) The information processing apparatus according to (3) described above, in which the data generation unit generates Adversarial Example on the basis of Fast Gradient Sign Method.

(5) The information processing apparatus according to any one of (1) to (4) described above, in which the data generation unit generates second learning data by superimposing noise on data included in the learning data.

(6) An information processing method including:

a step of inputting first learning data to be used for learning of a machine learning model;

a step of acquiring information regarding bias of the learning data;

a step of generating second learning data by using data included in the learning data on the basis of the information regarding bias; and a step of learning the machine learning model by using the first learning data and the second learning data.

(7) A computer program described in a computer-readable format to cause a computer to function as:

a data holding unit configured to hold first learning data to be used for learning of a machine learning model;

an acquisition unit configured to acquire information regarding bias of the learning data;

a data generation unit configured to generate second learning data by using data included in the learning data on the basis of the information regarding bias; and a learning unit configured to learn the machine learning model by using the first learning data and the second learning data.

(8) An imaging device including:

an imaging unit configured to capture an image; and a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

(9) The imaging device according to (8) described above, in which learning data is generated by using data of an image that is to be minority in the learning data in accordance with a field to which the imaging device is applied, and the machine learning model is learned by using the generated learning data.

(10) A vehicle device including:

an imaging device including a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

(11) A medical robot device including:

an imaging device including an imaging unit configured to capture an image around a surgical site, and a recognition unit configured to recognize the captured image by using a machine learning model, in which on the basis of information regarding bias of learning data for learning the machine learning model, the imaging device generates learning data by using data included in the learning data, and learns the machine learning model by using the generated learning data.

REFERENCE SIGNS LIST

100 Learning system
101 Learning data holding unit
102 Learning unit
103 Model parameter holding unit
104 Analysis unit
105 Data generation unit
111 Inference unit
112 Data input unit
113 Input data processing unit
800 Imaging device
801 Optical unit
802 Sensor unit
803 Sensor control unit
804 Recognition processing unit
805 Memory
806 Visual recognition processing unit
807 Output control unit
808 Display unit
1301 Pixel array unit
1302 Vertical scanning unit
1303 AD conversion unit
1304 Horizontal scanning unit
1305 Pixel signal line
1306 Control unit
1307 Signal processing unit
1310 Pixel circuit
1311 Column AD converter
1312 Reference signal generation unit
1500 In-vehicle camera
1501 Lens
1502 Image sensor
1503 Signal processing unit
1504 Recognition unit
1505 Control unit
1510 Vehicle control system
1601 Shutter
1602 Element unit
1603 Analog gain processing unit
1604 Development processing unit
1605 Detection unit
1606 Comparison unit
1800 Medical robot device
1810 Robot arm
1820 Control device
1821 Image recognizer
1822 Motion predictor

The invention claimed is:

1. An information processing apparatus, comprising:
circuitry configured to:
hold first learning data for a learning operation of a machine learning model;
acquire information regarding bias of the first learning data, wherein
the acquired information regarding the bias corresponds to a set of data associated with at least one specific attribute, and
the first learning data includes the set of data;
superimpose noise on the first learning data;
generate second learning data based on the superimposed noise on the first learning data and the information regarding the bias of the first learning data; and
execute, based on the generated second learning data and the held first learning data, the learning operation of the machine learning model.

2. The information processing apparatus according to claim 1, wherein the circuitry is further configured to:
acquire information indicating a minority attribute in the held first learning data; and
generate, further based on the information indicating the minority attribute, the second learning data, wherein the generated second learning data have a same attribute as the minority attribute.

3. The information processing apparatus according to claim 2, wherein
the circuitry is further configured to generate, based on the minority attribute, Adversarial Example as the second learning data.

4. The information processing apparatus according to claim 3, wherein
the circuitry is further configured to generate the Adversarial Example further based on a Fast Gradient Sign Method.

5. An information processing method, comprising:
storing first learning data for a learning operation of a machine learning model;
acquiring information regarding bias of the first learning data, wherein
the acquired information regarding the bias corresponds to a set of data associated with at least one specific attribute, and
the first learning data includes the set of data;
superimposing noise on the first learning data;
generating second learning data based on the superimposed noise on the first learning data and the information regarding the bias of the first learning data; and
executing, based on the generated second learning data and the stored first learning data, the learning operation of the machine learning model.

6. A non-transitory computer-readable medium having stored thereon, computer-executable instructions which, when executed by a computer, cause the computer to execute operations, the operations comprising:
holding first learning data for a learning operation of a machine learning model;
acquiring information regarding bias of the first learning data, wherein
the acquired information regarding the bias corresponds to a set of data associated with at least one specific attribute, and
the first learning data includes the set of data;
superimposing noise on the first learning data;
generating second learning data based on the superimposed noise on the first learning data and the information regarding the bias of the first learning data; and
executing, based on the generated second learning data and the held first learning data, the learning operation of the machine learning model.

7. An imaging device, comprising:
circuitry configured to:
hold first learning data for a learning operation of a machine learning model;
acquire information regarding bias of the first learning data, wherein the acquired information regarding the bias corresponds to a set of data associated with at least one specific attribute, and the first learning data includes the set of data;

superimpose noise on the first learning data;

generate second learning data based on the superimposed noise on the first learning data and the information regarding the bias of the first learning data;

execute, based on the generated second learning data and the held first learning data, the learning operation of the machine learning model;

capture an image; and recognize the captured image based on the machine learning model and the executed learning operation of the machine learning model.

8. The imaging device according to claim 7, wherein the circuitry is further configured to:

determine, based on a field associated with the imaging device, a minority in the first learning data; and generate the second learning data based on data of an image associated with the determined minority in the first learning data.

9. A vehicle device, comprising:

circuitry configured to:

hold first learning data for a learning operation of a machine learning model;

acquire information regarding bias of the first learning data, wherein the acquired information regarding the bias corresponds to a set of data associated with at least one specific attribute, and the first learning data includes the set of data;

superimpose noise on the first learning data;

generate second learning data based on the superimposed noise on the first learning data and the information regarding the bias of the first learning data;

execute, based on the generated second learning data and the held first learning data, the learning operation of the machine learning model;

capture an image in a vicinity of the vehicle device; and recognize the captured image based on the machine learning model and the executed learning operation of the machine learning model.

10. A medical robot device, comprising:

circuitry configured to:

hold first learning data for a learning operation of a machine learning model;

acquire information regarding bias of the first learning data, wherein the acquired information regarding the bias corresponds to a set of data associated with at least one specific attribute, and the first learning data includes the set of data;

superimpose noise on the first learning data;

generate second learning data based on the superimposed noise on the first learning data and the information regarding the bias of the first learning data;

execute, based on the generated second learning data and the held first learning data, the learning operation of the machine learning model;

capture an image in a vicinity of a surgical site; and recognize the captured image based on the machine learning model and the executed learning operation of the machine learning model.

* * * * *